(12) United States Patent
Nidam

(10) Patent No.: US 12,220,660 B2
(45) Date of Patent: Feb. 11, 2025

(54) AIR TREATMENT SYSTEMS AND METHODS

(71) Applicant: DUSMIT LTD, Kfar Hanagid (IL)

(72) Inventor: Ofer Nidam, Kfar Hanagid (IL)

(73) Assignee: DUSMIT LTD, Kfar Hanagid (IL)

( * ) Notice: Subject to any disclaimer, the term of this patent is extended or adjusted under 35 U.S.C. 154(b) by 0 days.

(21) Appl. No.: 18/012,070

(22) PCT Filed: Jun. 8, 2021

(86) PCT No.: PCT/IL2021/050682
§ 371 (c)(1),
(2) Date: Dec. 21, 2022

(87) PCT Pub. No.: WO2021/260677
PCT Pub. Date: Dec. 30, 2021

(65) Prior Publication Data
US 2023/0191320 A1    Jun. 22, 2023

Related U.S. Application Data

(60) Provisional application No. 63/093,217, filed on Oct. 18, 2020, provisional application No. 63/064,973,
(Continued)

(51) Int. Cl.
*A61L 9/16* (2006.01)
*A61L 9/03* (2006.01)
(Continued)

(52) U.S. Cl.
CPC ............. *B01D 53/343* (2013.01); *A61L 9/03* (2013.01); *A61L 9/16* (2013.01); *B01D 53/8687* (2013.01);
(Continued)

(58) Field of Classification Search
CPC ... A61L 9/03; A61L 9/032; A61L 9/16; B01D 53/343; B01D 53/8687; F24F 8/20
See application file for complete search history.

(56) References Cited

U.S. PATENT DOCUMENTS 3,858,645 A * 1/1975 Egger ...................... A61L 9/16
422/4
7,829,034 B2 11/2010 Ding
(Continued)

FOREIGN PATENT DOCUMENTS

CN    109200818 A  *  1/2019  ......... B01D 53/8687
CN    109999632 A     7/2019
(Continued)

OTHER PUBLICATIONS

Machine translation of CN109200818A (Year: 2019).*
Elsworth, et al. "Sterilization of Air by Heat." 1955. Epidemiology and Infection 53(4):445-57. (Year: 1955).*

*Primary Examiner* — Timothy C Cleveland
(74) *Attorney, Agent, or Firm* — Roach Brown McCarthy & Gruber P.C.; Kevin D. McCarthy

(57) ABSTRACT

One disclosed system includes: (a) a fan directing an initial air stream to a heater with sufficient heating capacity to heat said initial airstream to a temperature of 200° C. to 350° C. and output a heated air stream; and (b) an air to air heat exchanger positioned and configured to use said heated air stream to preheat said initial airstream prior to its arrival at said heater. Additional systems and corresponding methods are disclosed.

18 Claims, 12 Drawing Sheets

Related U.S. Application Data filed on Aug. 13, 2020, provisional application No. 63/043,141, filed on Jun. 24, 2020, provisional application No. 63/043,134, filed on Jun. 24, 2020, provisional application No. 63/043,140, filed on Jun. 24, 2020.

(51) Int. Cl.
　　*B01D 53/34*　　(2006.01)
　　*B01D 53/86*　　(2006.01)
　　*F24F 1/14*　　(2011.01)
　　*F24F 8/20*　　(2021.01)

(52) U.S. Cl.
　　CPC ................. *F24F 1/14* (2013.01); *F24F 8/20* (2021.01); *B01D 2251/108* (2013.01); *B01D 2257/708* (2013.01); *B01D 2258/06* (2013.01)

(56) References Cited

U.S. PATENT DOCUMENTS

| | | |
|---|---|---|
| 9,955,829 B2 | 5/2018 | Sifers et al. |
| 2009/0145140 A1 | 6/2009 | Shapiro |
| 2009/0293527 A1* | 12/2009 | Rakuma ................ C02F 1/4618 62/317 |
| 2013/0004376 A1 | 1/2013 | Ryou et al. |
| 2017/0143858 A1* | 5/2017 | Papadopoulos ........... C02F 1/06 |

FOREIGN PATENT DOCUMENTS

| | | |
|---|---|---|
| KR | 101 717 535 B1 | 3/2017 |
| WO | 2019239406 A1 | 12/2019 |

* cited by examiner

AIR TREATMENT SYSTEMS AND METHODS

CROSS-REFERENCE TO RELATED APPLICATIONS

This is a National Stage Application filed under 35 U.S.C. 371 based on International Patent Application No. PCT/IL2021/050682, filed on Jun. 8, 2021, which claims the benefit according to 35 U.S.C. § 119 (e) of U.S. provisional application 63/043,134 filed on Jun. 24, 2020 and entitled "Air Treatment Systems Including a Release Orifice"; and US provisional application 63/043,140 filed on Jun. 24, 2020 and entitled "Air Treatment Systems Including an Air to Air Heat Exchanger"; and U.S. provisional application 63/043,141 filed on Jun. 24, 2020 and entitled "Evaporative Cooling Air Treatment Systems"; and U.S. provisional application 63/064,973 filed on Aug. 13, 2020 and entitled "Air Treatment Systems and methods"; and U.S. provisional application 63/093,217 filed on Oct. 18, 2020 and entitled "Air Treatment Systems and methods". Each of these earlier applications is fully incorporated herein by reference.

FIELD OF THE INVENTION

The invention is in the field of air treatment.

BACKGROUND OF THE INVENTION

The recent COVID-19 pandemic has created an increased demand for air purification systems.

WO 2019/239406 describes systems for purifying air that rely on a combination of pressure and temperature to destroy airborne pathogens and/or allergens.

In addition to pathogens, there are many non-biological contaminants in air.

For example, volatile organic compounds (VOCs) are emitted as gases from certain solids or liquids. VOCs in air can have short- and long-term adverse health effects. Indoor concentrations of VOCs are typically as much as ten times higher than outdoor concentrations of the same compounds. The difference between indoor and outdoor VOC concentrations is because VOCs are emitted by a wide array of products including but not limited to paints and/or lacquers and/or paint strippers and/or cleaning supplies and/or pesticides and/or building materials and/or furnishings and/or office equipment (e.g. copiers and printers). In addition, many common school or office supplies emit VOCs. Examples include, but are not limited to correction fluids and/or carbonless copy paper and/or graphics and craft materials (e.g. glues and adhesives) and/or permanent markers.

SUMMARY OF THE INVENTION

One aspect of some embodiments of the invention relates to using heat in a stream of purified air to transform water to steam. In some embodiments, a heated flow of purified air is brought into contact with water. Optionally, the water is converted to steam which then dissolves in the stream of purified air (evaporative cooling).

In some embodiments, water used in the water spray is water that is removed from the air during the purification process. According to these embodiments, water content (humidity) of air entering an air purification system and leaving the system is about the same.

According to another aspect of some embodiments of the invention, air is purified at ambient atmospheric pressure. In some exemplary embodiments of the invention, a temperature applied to the air at ambient atmospheric pressure is 200° C.; 225° C.; 250° C.; 275° C.; 300° C.; 325° C. or intermediate or higher temperatures. Alternatively or additionally, in some embodiments a temperature applied to the air at ambient atmospheric pressure is 325° C.; 300° C.; 275° C.; 250° C.; 225° C.; 200° C. or intermediate or lower temperatures. In some embodiments, heat inactivates pathogens in the air. Alternatively or additionally, in some embodiments, heat is used to activate a catalytic oxidizer. In some embodiments, the catalytic oxidizer contributes to a reduction in volatile organic compounds (VOCs) in the air. Alternatively or additionally, in some embodiments, hypochlorous acid is mixed with an airstream as part of a purification process. In some embodiments, hypochlorous acid contributes to a reduction in volatile organic compounds (VOCs) in the air and/contributes to a reduction in an amount of active pathogens in the air. In some embodiments the hypochlorous acid is delivered in a spray of water.

Another aspect of some embodiments of the invention relates to electrolysis of salted water to produce hypochlorous acid. In some embodiments, at least a portion of the hypochlorous acid remains dissolved in water and the water is routed to a sprayer. In some exemplary embodiments of the invention, spraying of water containing hypochlorous acid into a stream of hot air contributes to a reduction in VOCs in the air. Alternatively or additionally, spraying of water containing hypochlorous acid into a stream of hot air contributes to a reduction in temperature and/or an increase in humidity of the air. According to various exemplary embodiments of the invention, the stream of air is an ambient pressure stream or a high-pressure stream.

Another aspect of some embodiments of the invention relates to use of a catalytic oxidizer to reduce VOCs in a heated air stream. According to various exemplary embodiments of the invention, the stream of air is an ambient pressure stream or a high-pressure stream.

Another aspect of some embodiments of the invention relates to using an Air to Air heat exchanger to transfer heat between 2 flows of compressed air. In some embodiments a heated flow of purified air is cooled prior to routing to a climate control system. Optionally, this cooling contributes to efficiency of the climate control system. Alternatively or additionally, in some embodiments a flow of compressed air is heated prior to purification by pressure which causes additional heating. Optionally, this preheating contributes to efficiency of the purification process.

In some embodiments compressed air with an initial temperature of 135° C. to 200° C. enters the heat exchanger and exits the heat exchanger at 20° C. to 50° C. above the initial temperature. Alternatively or additionally, in some embodiments a pressure tank further heats the air as part of a purification process.

In other exemplary embodiments of the invention, compressed air is cooled to remove excess water and enters the exchanger at 55° C. to 100° C. According to these embodiments the heat exchanger heats the compressed air to 150° C. to 200° C.

Still another aspect of some embodiments of the invention relates to using an orifice of fixed diameter to release pressurized air from an air treatment system. In some exemplary embodiments of the invention, a stream of purified air is cooled by releasing it through the orifice. In some embodiments internal energy is lost as the volume increases and heat energy is converted to kinetic energy. The orifice is a substitute for a valve. The orifice has no moving parts. The absence of moving parts contributes to an increase in durability and/or reliability and/or to a decrease in maintenance requirements, relative to a valve.

In some exemplary embodiments of the invention, a single aspect set forth above is employed. In other exemplary embodiments of the invention, two, three, four, five or more aspects are combined.

It will be appreciated that the various aspects described above relate to solution of technical problems associated with air purification. Specifically, some embodiments of the invention relate to technical problems associated with reducing VOC concentration in air.

Alternatively or additionally, it will be appreciated that the various aspects described above relate to solution of technical problems related to reducing the temperature of a stream of purified air sufficiently that it can be incorporated into the airstream of a climate control system without adversely affecting performance of the climate control system.

Alternatively or additionally, it will be appreciated that the various aspects described above relate to solution of technical problems related to maintaining relative humidity during air purification.

Alternatively or additionally, it will be appreciated that the various aspects described above relate to solution of technical problems related to reducing the energy burden on an air purification system.

In some exemplary embodiments of the invention there is provided a system including: (a) a fan directing an initial air stream to a heater with sufficient heating capacity to heat the initial airstream to a temperature of 200° C. to 350° C. and output a heated air stream; and (b) an air to air heat exchanger positioned and configured to use the heated air stream to preheat the initial airstream prior to its arrival at the heater. In some embodiments the system includes a cooling unit positioned to further cool the heated air stream after it passes through the air to air heat exchanger. Alternatively or additionally, in some embodiments the cooling unit includes one or more functional elements selected from the group consisting of a heat pump, an active heat exchanger and a passive heat exchanger. Alternatively or additionally, in some embodiments the system includes an evaporative cooler comprising a water source. Alternatively or additionally, in some embodiments the evaporative cooler is positioned to receive the heated air stream. Alternatively or additionally, in some embodiments the evaporative cooler is positioned to receive the heated air stream after the heated air stream has passed through the air to air heat exchanger. Alternatively or additionally, in some embodiments the evaporative cooler is positioned to receive the initial air stream as it exits the fan. Alternatively or additionally, in some embodiments the system includes a catalytic oxidizer positioned between an exit of the heater and the air to air heat exchanger so that the heated air stream flows through the catalytic oxidizer producing a VOC reduced hot air stream. Alternatively or additionally, in some embodiments the system includes a channel of fluid communication routing water from a water reservoir to the water source; and a pump configured to move the water through the channel of fluid communication to the water source. Alternatively or additionally, in some embodiments the system includes an electrolytic element in the water reservoir. Alternatively or additionally, in some embodiments the system includes a source of hypochlorous acid.

Alternatively or additionally, in some embodiments the air to air heat exchanger preheats the initial airstream from room temperature to at least 150° C. within 1 second. Alternatively or additionally, in some embodiments the heater heats the initial airstream to at least 200° C. within 0.5 seconds to 1 second. Alternatively or additionally, in some embodiments the heater heats the initial airstream to at least 350° C. within 1 second. Alternatively or additionally, in some embodiments the heated air stream passing through the heat exchanger is cooled within 1 second as it heats the initial airstream. Alternatively or additionally, in some embodiments the heater has a retention time of at least 5 seconds. In some embodiments baffles contribute to an increase in retention time. Alternatively or additionally, in some embodiments the heated air stream output by the heater arrives at the heat exchanger at least 2 seconds after exiting the heater.

In some exemplary embodiments of the invention there is provided an air purification system including: (a) a compressor and a pressure tank providing an output flow stream of heated pressurized air; and (b) a water delivery mechanism configured and positioned to deliver water into the output flow stream of pressurized air. In some embodiments the water delivered by the water delivery mechanism comprises condensate from the compressor. Alternatively or additionally, in some embodiments the water delivered by the water delivery mechanism comprises hypochlorous acid. Alternatively or additionally, in some embodiments the system includes a channel of fluid communication routing water from a condensate collector pan of the compressor to the water delivery mechanism; and a pump configured to move the water through the channel of fluid communication to the water delivery mechanism. Alternatively or additionally, in some embodiments the system includes an electrolytic element in the condensate collector pan of the compressor. Alternatively or additionally, in some embodiments the system includes a catalytic oxidizer positioned to receive the output flow stream of pressurized air. Alternatively or additionally, in some embodiments the system includes a UV lamp irradiating water in the condensate collector pan. Alternatively or additionally, in some embodiments a temperature of the output flow stream of pressurized air is at least 200° C. Alternatively or additionally, in some embodiments a pressure of the output flow stream of pressurized air is at least 4 atmospheres. Alternatively or additionally, in some embodiments the pressure tank heats air to at least 200° C. within 0.5 seconds to 1 second. Alternatively or additionally, in some embodiments the pressure tank heats said air to at least 350° C. within 1 second. Alternatively or additionally, in some embodiments the pressure tank has a retention time of at least 5 seconds.

In some exemplary embodiments of the invention there is provided an air purification system including: (a) a compressor and a pressure tank providing an initial output flow stream of heated pressurized air; (b) a catalytic oxidizer positioned to receive the initial output flow stream of pressurized air and produce a modified output flow stream; and (c) a water delivery mechanism configured and positioned to deliver water into the modified output flow stream. In some exemplary embodiments of the invention there is provided an air purification system including: (a) a compressor and a pressure tank providing an initial output flow stream of heated pressurized air; (b) a catalytic oxidizer positioned to receive the initial output flow stream of pressurized air and produce a modified output flow stream; and (c) a water delivery mechanism configured and positioned to deliver water into the initial flow stream of heated pressurized air. In some embodiments of these systems the water delivered by the water delivery mechanism comprises condensate from the compressor. Alternatively or additionally, in some embodiments of these systems the water delivered by the water delivery mechanism comprises hypochlorous acid. Alternatively or additionally, in some embodiments these systems include a channel of fluid communication routing water from a condensate collector pan of the compressor to the water delivery mechanism; and a pump configured to move the water through the channel of fluid communication to the water delivery mechanism. Alternatively or additionally, in some embodiments these systems include an electrolytic element in the condensate collector pan of the compressor. Alternatively or additionally, in some embodiments these systems include a UV lamp irradiating water in the condensate collector pan. Alternatively or additionally, in some embodiments of these systems a temperature of the output flow stream of pressurized air is at least 200° C. Alternatively or additionally, in some embodiments of these systems a pressure of the output flow stream of pressurized air is at least 4 atmospheres. Alternatively or additionally, in some embodiments the pressure tank heats air to at least 200° C. within 0.5 seconds to 1 second. Alternatively or additionally, in some embodiments the pressure tank heats said air to at least 350° C. within 1 second. Alternatively or additionally, in some embodiments the pressure tank has a retention time of at least 5 seconds.

In some exemplary embodiments of the invention there is provided a method including: (a) neutralizing volatile organic compounds in a flow stream of heated air with a catalytic oxidizer; and (b) using heat energy from the flow stream to convert water into steam. In some embodiments the stream of heated air is pressurized to at least 1.9 atmospheres.

In some exemplary embodiments of the invention there is provided a system including: (a) a dehumidifier producing a dehumidified air stream; (b) a heater with sufficient heating capacity to heat the dehumidified airstream to a temperature of 200° C. to 350° C. and output a heated air stream; (c) an air to air heat exchanger positioned and configured to use the heated air stream to preheat the dehumidified airstream prior to its arrival at the heater; and (d) an evaporative cooler. In some embodiments the evaporative cooler is positioned to receive the heated air stream after the heated air stream has passed through the air to air heat exchanger and comprising a water source. Alternatively or additionally, in some embodiments the evaporative cooler is positioned to receive the heated air stream. Alternatively or additionally, in some embodiments the system includes a catalytic oxidizer positioned between an exit of the heater and the air to air heat exchanger so that the heated air stream flows through the catalytic oxidizer producing a VOC reduced hot air stream. Alternatively or additionally, in some embodiments the system includes a channel of fluid communication routing water from a condensate collector pan of the dehumidifier to the water source; and a pump configured to move the water through the channel of fluid communication to the water source. Alternatively or additionally, in some embodiments the system includes an electrolytic element in the condensate collector pan of the dehumidifier. Alternatively or additionally, in some embodiments the system includes a source of hypochlorous acid. Alternatively or additionally, in some embodiments the air to air heat exchanger preheats the dehumidified air from room temperature to at least 150° C. within 1 second. Alternatively or additionally, in some embodiments the heater heats the dehumidified airstream to at least 200° C. within 0.5 seconds to 1 second. Alternatively or additionally, in some embodiments the heater heats the dehumidified airstream to at least 350° C. within 1 second.

Alternatively or additionally, in some embodiments the heated air stream passing through the heat exchanger is cooled within 1 second as it heats the dehumidified airstream. Alternatively or additionally, in some embodiments the heater has a retention time of at least 5 seconds. Alternatively or additionally, in some embodiments the heated air stream output by said heater arrives at said heat exchanger at least 2 seconds after exiting said heater.

In some exemplary embodiments of the invention there is provided a method including: (a) dehumidifying and heating air to a temperature of at least 200° C.; (b) reducing a concentration of VOCs in the air by at least 90%; and (c) cooling and re-humidifying the air.

In some exemplary embodiments of the invention there is provided a method including: (a) humidifying and heating air to a temperature of at least 200° C.; (b) reducing a concentration of VOCs in the air by at least 90%; and (c) cooling and dehumidifying the air.

In some exemplary embodiments of the invention there is provided a method including: (a) dispersing aqueous hypochlorous acid in an air stream with a temperature of at least 100° C.; and (b) routing the air stream to a catalytic oxidizer.

In some exemplary embodiments of the invention there is provided a method including: (a) using heat energy from a flow stream of heated pressurized air to convert water into steam; and (b) dissolving the steam in the air to humidify it.

In some exemplary embodiments of the invention there is provided an air purification system including: (a) a compressor providing a first output flow of pressurized air at a first temperature; (b) a pressure tank providing a second output flow of pressurized air at a second higher temperature; and (c) an air to air heat exchanger designed and configured to heat the first output flow using heat from the second output flow. In some embodiments the first temperature is at ambient temperature plus 25° C. Alternatively or additionally, in some embodiments the second temperature is 120° C. to 190° C. Alternatively or additionally, in some embodiments the pressurized air is at a pressure of at least 1.9 atmospheres. Alternatively or additionally, in some embodiments the air to air heat exchanger preheats said pressurized air from room temperature to at least 150° C.; 160° C.; 170° C.; 180° C. or intermediate or higher temperatures within 1 second. Alternatively or additionally, in some embodiments the pressure tank heats the pressurized airstream to at least 200° C. within 0.5 seconds to 1 second. Alternatively or additionally, in some embodiments the pressure tank heats said pressurized airstream to at least 350° C. within 1 second. Alternatively or additionally, in some embodiments the heated air stream passing through said heat exchanger is cooled within 1 second as it heats said pressurized airstream. Alternatively or additionally, in some embodiments the pressure tank has a retention time of at least 5 seconds. Alternatively or additionally, in some embodiments heated air stream output by the pressure tank arrives at the heat exchanger after at least 2 seconds.

In some exemplary embodiments of the invention there is provided a method including: pressurizing airstreams directed to an air to air heat exchanger in an air treatment system. In some embodiments the pressurizing is to a pressure of at least 1.9 atmospheres.

In some exemplary embodiments of the invention there is provided an air purification system including: (a) a compressor providing an output flow of pressurized air to a pressure tank which heats the air while maintaining pressure; and (b) a release manifold having a partially closed end including an orifice, the manifold in fluid communication with the pressure tank.

In some exemplary embodiments of the invention there is provided a method including: routing a pressurized air stream at a temperature of at least 30° C. through a fixed diameter orifice to cool the stream. In some embodiments the temperature does not exceed 70° C. Alternatively or additionally, in some embodiments passage through the orifice cools the stream to 25° C. or less.

For purposes of this specification and the accompanying claims, the term "impurities" includes, but is not limited to, airborne pathogens and/or VOCs. As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office. Thus, any recitation that an embodiment "includes" or "comprises" a feature is a specific statement that sub embodiments, "consist essentially of" and/or "consist of" the recited feature.

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The phrase "adapted to" as used in this specification and the accompanying claims imposes additional structural limitations on a previously recited component.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

Implementation of the method and system according to embodiments, of the invention involves performing or completing selected tasks or steps manually, automatically, or a combination thereof. Moreover, according to actual instrumentation and equipment of exemplary embodiments, of methods, apparatus and systems of the invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

In order to understand the invention and to see how it may be carried out in practice, embodiments, will now be described, by way of non-limiting example only, with reference to the accompanying figures. In the figures, identical and similar structures, elements or parts thereof that appear in more than one figure are generally labeled with the same or similar references in the figures in which they appear.

Dimensions of components and features shown in the figures are chosen primarily for convenience and clarity of presentation and are not necessarily to scale. The attached figures are.

DETAILED DESCRIPTION OF EMBODIMENTS

Embodiments of the invention relate to air purification systems and methods.

Specifically, some embodiments of the invention are used to re-humidify air in an air purification system and/or reduce the heating burden on a climate control system receiving purified air from the system. Alternatively or additionally, some embodiments of the invention are used to reduce a concentration of VOCs in the air and/or to inactivate airborne pathogens.

The principles and operation of an air purification system and method according to exemplary embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Exemplary High Pressure System

Figure 1A:
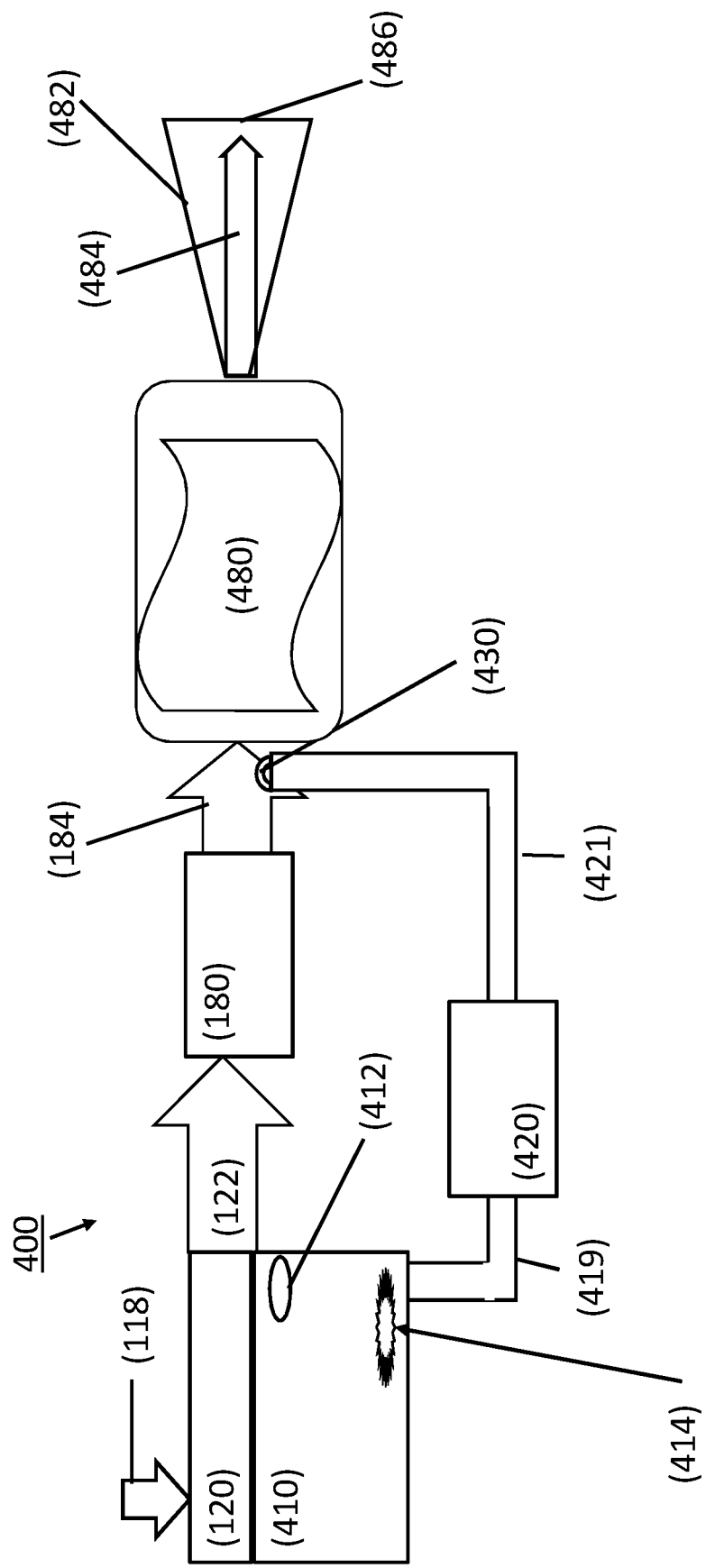
FIG. 1A is a simplified schematic representation of an air purification system according to some exemplary embodiments of the invention.

FIG. 1A is simplified schematic representation of an air purification system, indicated generally as 400, according to some exemplary embodiments of the invention.

Depicted exemplary air purification system 400 includes a compressor 120 and a pressure tank 180 providing an output flow stream 184 of heated pressurized air. In the depicted embodiment, compressor 120 draws in ambient air 118, which carries one or more types of impurities. Compressor 120 produces a pressurized airstream 122 that is conveyed to pressure tank 180.

According to various exemplary embodiments of the invention airstream 122 has a pressure of 1.9 atmospheres; 3 atmospheres; 4 atmospheres; 5 atmospheres; 6 atmospheres; 7 atmospheres; 8 atmospheres; 9 atmospheres; 10 atmospheres or intermediate pressures. In some embodiments airstream 122 has a pressure of 8 to 10 atmospheres. Although airstream 122 is depicted as an arrow, it is typically directed by a pipe or other conduit to pressure tank 180.

In the depicted embodiment, system 400 includes a pressure tank 180 which receives output airstream 122 of pressurized air and heats the air while maintaining pressure. In some exemplary embodiments of the invention, pressure tank 180 heats the air to a temperature of 170° C.; 180° C.; 190° C.; 200° C.; 210° C.; 220° C.; 230° C.; 240° C.; 250° C. or intermediate or higher temperature. Alternatively or additionally, in some embodiments pressure tank 180 heats the air to a target temperature for 1 seconds, 2 seconds, 3 seconds, 4 seconds, 5 seconds, 6 seconds, 7 seconds, 8 seconds, 9 seconds, 10 seconds, 11 seconds, 12 seconds, 20 seconds, 30 seconds, 40 seconds, 50 seconds, or 60 seconds or intermediate or longer amounts of time. In some embodiments, a temperature of output flow stream 184 of pressurized air is at least 200° C. Alternatively or additionally, in some embodiments a pressure of said output flow stream of pressurized air is at least 1.9 atmospheres or at least 4 atmospheres.

In the depicted embodiment, system 400 includes a water delivery mechanism 430 configured and positioned to deliver water into output flow stream 184 of pressurized air. In the depicted embodiment, the water delivery mechanism 430 is a sprayer. In other exemplary embodiments of the invention, water delivery mechanism 430 is a nebulizer or wick/evaporative device.

In the depicted embodiment, water delivered by water delivery mechanism 430 comprises condensate from compressor 120. In the depicted embodiment, condensate from compressor 120 collects in a collection pan 410 and is pumped by a pump 420 trough pipes 419 and 421 to water delivery mechanism 430. Pipes 419 and/or 421 provide a channel of fluid communication. In some embodiments a UV lamp 412 shines on water in pan 410. In some embodiments UV irradiation inactivates microorganisms in the water (e.g. bacteria and/or virus particles).

In some exemplary embodiments of the invention, water delivered by water delivery mechanism 430 contains hypochlorous acid. In some exemplary embodiments of the invention, condensate collector pan 410 contains an electrolytic element 414. According to these embodiments salt placed in water in pan 410 produces hypochlorous acid as a result of electrolysis. In other exemplary embodiments of the invention, hypochlorous acid is provided from an external source. In some exemplary embodiments of the invention, water delivered to stream 184 by mechanism 430 is converted to steam by heat energy in stream 184. In some embodiments conversion of water to steam cools the air in stream 184.

In the depicted embodiment, system 400 includes a catalytic oxidizer 480 positioned to receive the output flow stream 184. In some embodiments a higher temperature of stream 184 contributes to an increase in oxidation by catalytic oxidizer 480.

In other exemplary embodiments of the invention, (not depicted) water delivered by mechanism 430 is from an external water source.

In other exemplary embodiments of the invention, (not depicted) water extracted from treated air (e.g. by a dehumidifier) is delivered by mechanism 430. According to various exemplary embodiments of the invention the dehumidifier is desiccant or thermoelectric based. According to these embodiments water provided by contributes to an increase in the evaporative cooling effect.

In some embodiments a temperature of output flow stream 184 is at least 100° C.; at least 110° C., least 120° C.; at least 130° C. least 140° C.; at least 150° C. least 160° C.; at least 170° C. least 180° C.; at least 190° C. least 200° C.; at least 210° C. least 220° C.; at least 230° C. least 240° C.; at least 250° C. least 260° C.; at least 270° C. least 100° C.; at least 280° C. least 290° C.; at least 300° C. or intermediate or greater temperatures. Alternatively or additionally, in some embodiments a pressure of output flow stream 184 is at least 1.9 atmospheres, at least 4 atmospheres, at least 5 atmospheres, at least 6 atmospheres, at least 7 atmospheres, at least 8 atmospheres, at least 9 atmospheres, at least 10 atmospheres or intermediate or greater pressures. In some exemplary embodiments of the invention, catalytic oxidizer 480 is dimensions similar to a pipe conducting stream 18 so there is no change in volume or pressure of the air as it passes from 184 to 480.

In the depicted embodiment, catalytic oxidizer 480 discharges a stream 484 through a wide end 486 of funnel 482. According to various exemplary embodiments of the invention the amount of VOCs in stream 484 relative to stream 184 is reduced by 90%; 95%; 99%; 99.5% or substantially 100% or intermediate percentages. According to various exemplary embodiments of the invention hypochlorous acid delivered by mechanism 430 and/or catalytic oxidizer 480 contribute to the reduction in VOC concentration. Alternatively or additionally, According to various exemplary embodiments of the invention the amount of active pathogens in stream 184 relative to ambient air 118 is reduced by 90%; 95%; 99%; 99.5% or substantially 100% or intermediate percentages. According to various exemplary embodiments of the invention the combination of pressure and temperature in 120 and/or 180 contributes to this reduction.

Exothermic reactions of VOCs in catalytic oxidizer 480 contribute to an increase in temperature. However, heat dissipation is always present (e.g. though walls of oxidizer 480) and if VOC concentration is low enough temperature of stream 484 exiting oxidizer 480 can be lower than stream 184 entering oxidizer 480.

The pressure of stream 484 is expected to be the same as stream 184 in oxidizer 480 and to return to ambient pressure as stream 484 exits an orifice in distal end 486 of exit conduit 482.

According to various exemplary embodiments of the invention a heat exchanger and/or other heat recovery elements to reduce air temperature are provided to reduce a temperature of stream 484. According to various exemplary embodiments of the invention as stream 484 approaches distal end 486 of exit conduit 482 air temperature is 30° C., 40° C., 50° C. or intermediate or lower temperatures. Alternatively or additionally, in some exemplary embodiments of the invention as stream 484 approaches distal end 486 of exit conduit 482, relative humidity will be 100% or more with water condensing in conduit 482. As stream 484 exits an orifice in 486, water in the air will boil as a result of the reduction in pressure. In some exemplary embodiments of the invention, pressure tank 180 heats air in stream 122 to at least 200° C. within 0.5 seconds to 1 second. Alternatively or additionally, in some embodiments pressure tank 180 heats air in stream 122 to at least 350° C. within 1 second. Alternatively or additionally, in some embodiments pressure tank 180 has a retention time of at least 5 seconds. In some embodiments baffles in tank 180 contribute to an increase in retention time.

Additional Exemplary High Pressure System

Figure 1B:
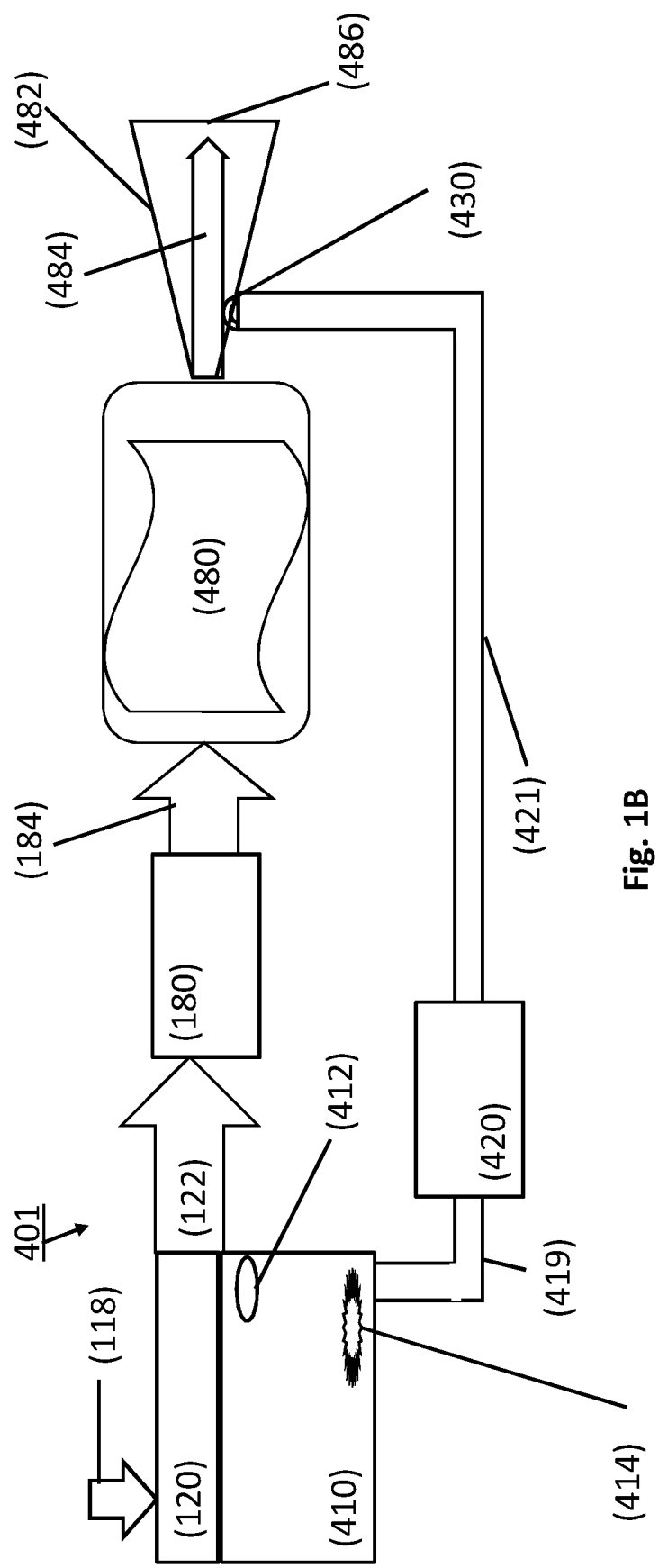
FIG. 1B is a simplified schematic representation of an air purification system according to some additional exemplary embodiments of the invention.

FIG. 1B is simplified schematic representation of an air purification system, indicated generally as 401, according to some exemplary embodiments of the invention.

Depicted exemplary air purification system 401 includes a compressor 120 and a pressure tank 180 providing an output flow stream 184 of heated pressurized air. In the depicted embodiment, compressor 120 draws in ambient air 118, which carries one or more types of impurities. Compressor 120 produces a pressurized airstream 122 that is conveyed to pressure tank 180.

According to various exemplary embodiments of the invention airstream 122 has a pressure of 1.9 atmospheres; 3 atmospheres; 4 atmospheres; 5 atmospheres; 6 atmospheres; 7 atmospheres; 8 atmospheres; 9 atmospheres; 10 atmospheres or intermediate pressures. In some embodiments airstream 122 has a pressure of 8 to 10 atmospheres. Although airstream 122 is depicted as an arrow, it is typically directed by a pipe or other conduit to pressure tank 180.

In the depicted embodiment, system 401 includes a pressure tank 180 which receives output airstream 122 of pressurized air and heats the air while maintaining pressure as described above in the context of FIG. 1A. Pressure tank 180 outputs a pressurized heated airstream 184. In some embodiments, a temperature of output airstream 184 is at least 200° C.

Alternatively or additionally, in some embodiments a pressure of said output flow stream of pressurized air is at least 1.9 atmospheres or at least 4 atmospheres.

In the depicted embodiment, system 401 includes a catalytic oxidizer 480 positioned to receive the output flow stream 184.

The main difference between systems 400 and 401 is the position of water delivery mechanism 430. In system 400, position of 430 is before 480. In system 401, position of 430 is after 480.

Referring again to FIG. 1B, in some embodiments system 401 includes a compressor 120 and a pressure tank 180 providing an initial output flow stream 184 of heated pressurized air and a catalytic oxidizer 480 positioned to receive said initial output flow stream 184 of pressurized air and produce a modified output flow stream 484. In some embodiments system 401 includes a water delivery mechanism 430 configured and positioned to deliver water into said initial flow stream 184 of heated pressurized air as depicted in FIG. 1A.

In some embodiments aqueous hypochlorous acid delivered at 430 after 480 contributes to a decrease in temperature of exit stream 484. A reduction in temperature of exit stream 484 can be an advantage.

Alternatively, in some embodiments aqueous hypochlorous acid delivered at 430 before 480 is oxidized at 480 so the air in exit 484 contains less hypochlorous acid. A reduction in hypochlorous acid concentration in exit stream 484 can be an advantage.

As described above in the context of FIG. 1A, catalytic oxidizer contributes to a reduction of VOCs in airstream 484 relative to 184.

In the depicted embodiment, system 401 includes a water delivery mechanism 430 configured and positioned to deliver water into output flow stream 484 of the system. In the depicted embodiment, the water delivery mechanism 430 is a sprayer. In other exemplary embodiments of the invention, the water delivery mechanism is a nebulizer or wick/evaporative device.

In the depicted embodiment, water delivered by water delivery mechanism 430 comprises condensate from compressor 120. In the depicted embodiment, condensate from compressor 120 collects in a collection pan 410 and is pumped by a pump 420 through pipes 419 and 421 to water delivery mechanism 430. Pipes 419 and/or 421 provide a channel of fluid communication. In some embodiments a UV lamp 412 shines on water in pan 410. In some embodiments UV irradiation inactivates microorganisms in the water (e.g. bacteria and/or virus particles).

In some exemplary embodiments of the invention, water delivered by water delivery mechanism 430 contains hypochlorous acid. According to these embodiments, the hypochlorous acid contributes to a reduction of VOCs in airstream 484. In some exemplary embodiments of the invention, condensate collector pan 410 contains an electrolytic element 414. According to these embodiments salt placed in water in pan 410 produces hypochlorous acid as a result of electrolysis. In other exemplary embodiments of the invention, hypochlorous acid is provided from an external source. In some exemplary embodiments of the invention, water delivered to stream 484 by mechanism 430 is converted to steam by heat energy in stream 484. According to these embodiments, conversion of water to steam cools the air in stream 484.

In other exemplary embodiments of the invention, (not depicted) water delivered by mechanism 430 is from an external water source.

In other exemplary embodiments of the invention, (not depicted) water extracted from treated air (e.g. by a dehumidifier) is delivered by mechanism 430. According to various exemplary embodiments of the invention the dehumidifier is desiccant or thermoelectric based.

In some embodiments a temperature of output flow stream 184 is at least 100° C.; at least 110° C., least 120° C.; at least 130° C. least 140° C.; at least 150° C. least 160° C.; at least 170° C. least 180° C.; at least 190° C. least 200° C.; at least 210° C. least 220° C.; at least 230° C. least 240° C.; at least 250° C. least 260° C.; at least 270° C. least 100° C.; at least 280° C. least 290° C.; at least 300° C. or intermediate or greater temperatures. Alternatively or additionally, in some embodiments a pressure of output flow stream 184 is at least 1.9 atmospheres, at least 4 atmospheres, at least 5 atmospheres, at least 6 atmospheres, at least 7 atmospheres, at least 8 atmospheres, at least 9 atmospheres, at least 10 atmospheres or intermediate or greater pressures.

Again, exothermic reactions of VOCs in catalytic oxidizer 480 contribute to an increase in temperature. However, heat dissipation is always present (e.g. though walls of oxidizer 480) and if VOC concentration is low enough temperature of stream 484 exiting oxidizer 480 can be lower than stream 184 entering oxidizer 480.

In some exemplary embodiments of the invention, pressure tank 180 heats air in stream 122 to at least 200° C. within 0.5 seconds to 1 second. Alternatively or additionally, in some embodiments pressure tank 180 heats air in stream 122 to at least 350° C. within 1 second. Alternatively or additionally, in some embodiments pressure tank 180 has a retention time of at least 5 seconds. In some embodiments baffles in tank 180 contribute to an increase in retention time.

Exemplary Low Pressure System

Figure 2A:
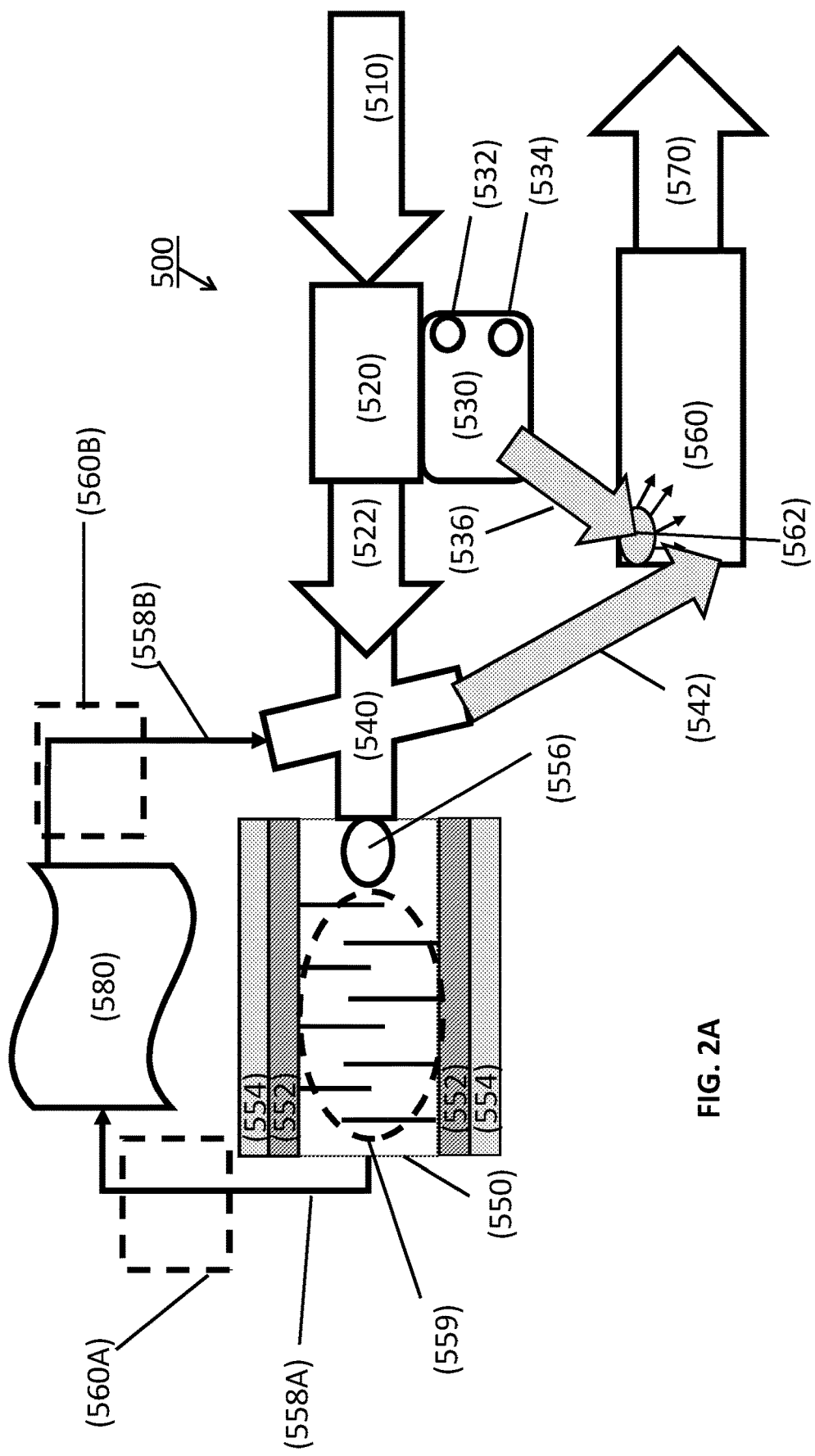
FIG. 2A is a simplified schematic representation of an air purification system according to some further additional exemplary embodiments of the invention.

FIG. 2A is a simplified schematic representation of an air purification system, indicated generally as 500, according to some further additional exemplary embodiments of the invention.

In the depicted embodiment, system 500 includes a dehumidifier 520 producing a dehumidified air stream 522. Dehumidifier 520 receives ambient air 510, which carries one or more types of impurities.

Depicted exemplary system 500 includes a heater with sufficient heating capacity to heat dehumidified airstream 522 to a temperature of 200° C. to 350° C. and output a heated air stream 558A. According to various exemplary embodiments of the invention heated air stream 558A has a temperature greater than 200° C.; greater than 225° C.; greater than 250° C.; greater than 275° C.; greater than 300° C.; greater than 325° C.; greater than 350° C. or intermediate or greater temperatures. Alternatively or additionally, in some embodiments of the invention heated air stream 558A has a temperature less than 350° C.; less than 325° C.; less than 300° C.; less than 275° C.; less than 250° C.; less than 225° C.; less than 200° C.; less than 175° C.; or intermediate or lower temperatures.

In the depicted embodiment, the heater includes heating element 556 and/or heating elements 552 of denaturation chamber 550. Some exemplary embodiments of the invention, the system include either 556 or 552. In other exemplary embodiments of the invention, the system includes both 556 and 552.

In some embodiments heating element 556 and/or 552 of the heater employ recovered heat from an outside source.

In the depicted embodiment, denaturation chamber 550 also includes insulation layer 554 and baffles 559. In some embodiments insulation layer 554 contributes to denaturation efficiency of chamber 550 by reducing heat loss from heating elements 552 and/or 556. Alternatively or additionally, in some embodiments baffles 559 contribute to denaturation efficiency of chamber 550 by increasing a length of a flow path in chamber 550. In some embodiments an increase in flow path length contributes to an increase in residence time for air in the chamber. Alternatively or additionally, in some embodiments baffles 559 are constructed from a material with high heat conductivity such as copper. According to these embodiments increasing a heated surface area within denaturation chamber 550 contributes to an increase in efficiency of heat transfer to air entering the chamber.

In some embodiments system 500 includes an air to air heat exchanger 540 positioned and configured to use the heated air stream 558B to preheat dehumidified airstream 522 prior to its arrival at heater (e.g. 556 and/or 552).

In some embodiments system 500 includes an evaporative cooler 560 receiving the heated air stream 542 after said heated air stream has passed through said air to air heat exchanger and comprising a water source 562. Water source 562 is depicted as a sprayer although nebulizers and/or wick evaporation elements are used in other embodiments of the invention.

Alternatively or additionally, in some embodiments system 500 includes an evaporative cooler 560A receiving the heated air stream 558A. In some embodiments a water source (not depicted) in 560A provides water which is evaporated by heat in stream 558A, cooling the stream as it enters catalytic oxidizer 580. In some embodiments a water source (not depicted) in an evaporative cooler 560B provides water which is evaporated by heat in stream 558B, cooling the stream as it leaves catalytic oxidizer 580. According to various exemplary embodiments of the invention the water source(s) include(s) a sprayer and/or nebulizers and/or wick evaporation element. According to various exemplary embodiments of the invention water added at 560 and/or 560A and/or 560B evaporates at 560 and cools the air.

In some exemplary embodiments of the invention, the same water is evaporated, condensed and evaporated a second time. For example, in FIG. 1A water added by 430 is evaporated by heat in stream 184, condenses in 482, then evaporates again as it passes through an orifice in 486. As another example, in FIG. 1B, water added by 430 is evaporated by heat in stream 484, condenses in 482, then evaporates again as it passes through an orifice in 486

In some embodiments a flow of air from 522 to 540 through 550, 558A, 558B, 540, 542 and 560 is continuous so long as the system is "on". Alternatively or additionally, in some embodiments evaporative cooler 560 restores the humidity level and/or temperature in exit air stream 570 to the level of humidity and/or temperature in ambient air 510.

In the depicted embodiment, system 500 includes a catalytic oxidizer 580 positioned (i.e. between 558A and 558B) between an exit of heater (chamber 550) and air to air heat exchanger 540 so that heated air stream 558A flows through catalytic oxidizer 580 producing a VOC reduced hot air stream 558B. In some embodiments exothermic reactions in 580 contribute to an increase in temperature of air stream 558 B relative to 558A.

Alternatively or additionally, in some embodiments system 500 includes a channel of fluid communication 536 routing water from a condensate collector pan 530 of dehumidifier 520 to water source 562. According to these embodiments, a pump (not depicted) is configured to move the water through channel of fluid communication 536 to water source 562. In the depicted embodiment, condensate pan 530 includes a UV light source 532. In some embodiments UV radiation from light source 532 neutralizes biological contaminants in water collecting in the pan.

Alternatively or additionally, in some embodiments pan 530 contains an electrolytic element 534. According to these embodiments, salt placed in water in pan 530 produces hypochlorous acid as a result of electrolysis. In some embodiments hypochlorous acid delivered in water sprayed from water source 562 contributes to a reduction in VOCs in stream 542 entering evaporative cooler 560.

In other exemplary embodiments of the invention, hypochlorous acid is delivered to water source 562 from an external source (not depicted).

Alternatively or additionally, in some embodiments the air to air heat exchanger 540 preheats the dehumidified air 522 from room temperature to at least 150° C. within 1 second. Alternatively or additionally, in some embodiments heater (denaturatiuon chamber) 550 heats dehumidified airstream 522 (after passing through 540) to at least 200° C. within 0.5 seconds to 1 second. Alternatively or additionally, in some embodiments heater 550 heats dehumidified airstream 522 to at least 350° C. within 1 second. Alternatively or additionally, in some embodiments heated air stream 558B passing through heat exchanger 540 is cooled within 1 second as it heats dehumidified airstream 522. Alternatively or additionally, in some embodiments heater 550 has a retention time of at least 5 seconds. In some embodiments baffles 559 contribute to retention time. Alternatively or additionally, in some embodiments the heated air stream 558A output by heater 550 arrives at said heat exchanger 540 at least 2 seconds after exiting heater 550 (see 558B).

Additional Exemplary Low Pressure Systems

Figure 2B:
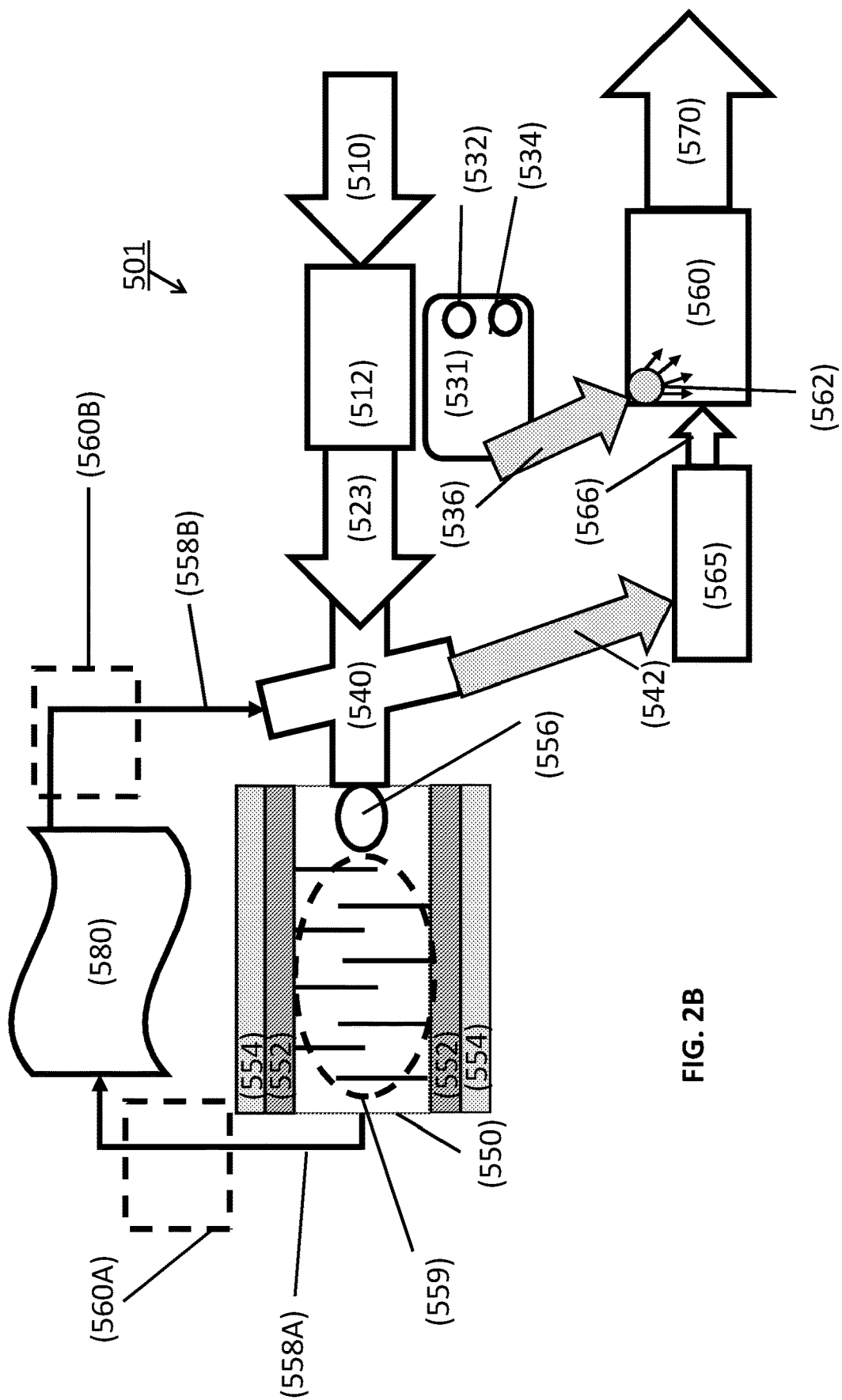
FIG. 2B is a simplified schematic representation of an air purification system according to some further additional exemplary embodiments of the invention.

FIG. 2B is a simplified schematic representation of an air purification system, indicated generally as 501, according to some further additional exemplary embodiments of the invention. Depicted exemplary system 501 includes a fan 512 which takes in input air 510 and directs an initial air stream 523 to a heater 556 and/or 552 with sufficient heating capacity to heat airstream 523 to a temperature of 200° C. to 350° C. and output a heated air stream 558A. According to various exemplary embodiments of the invention stream 558A has temperatures as described above.

Alternatively or additionally, in some embodiments a fan is positioned at 542. According to these embodiments, the fan "pulls" air from heat exchanger 540 and this negative pressure is transmitted all the way back to 523.

In some embodiments heating element 556 and/or 552 of the heater employ recovered heat from an outside source.

In the depicted embodiment, system 501 includes an air to air heat exchanger 540 positioned and configured to use heated air stream 5586 to preheat initial airstream 523 prior to its arrival at the heater 556 and/or 552.

In the depicted embodiment, system 501 includes a cooling unit 565 positioned to further cool heated air stream 542 after it passes through air to air heat exchanger 540 to produce output air 570.

According to various exemplary embodiments of the invention cooling unit 565 includes functional elements such as a heat pump and/or an active heat exchanger and/or a passive heat exchanger. Alternatively or additionally, in some embodiments cooling unit 565 employs cooling capability from an outside source such as a chiller. Alternatively or additionally, in some embodiments cooling unit 565 employs cold air from the surrounding to cool airstream 542 and/or 566, and/or uses the ground as a heat sink to absorb heat from airstream 542 and/or 566, and/or bubbles airstream 542 and/or 566 through water as a way to cool the air in the stream.

Alternatively or additionally, in some embodiments system 501 includes an evaporative cooler 560 comprising a water source 562 as described hereinabove. In some embodiments the evaporative cooler is positioned to receive said heated air stream 558A or 5586 (depicted schematically as 560(A) and 560(B))

In the depicted embodiment, evaporative cooler 560 is positioned to receive air stream 566 after it has passed through air to air heat exchanger 540 and/or cooling unit 565. In some embodiments evaporative cooler 560 is provided as part of cooling unit 565.

In the depicted embodiment, system 501 includes a catalytic oxidizer 580 positioned between an exit of the heater and air to air heat exchanger 540 so that heated air stream 558A flows through catalytic oxidizer 580 producing a VOC reduced hot air stream 558B.

In the depicted embodiment, system 501 includes a channel of fluid communication 536 routing water from a water reservoir 531 to water source 562 and a pump (not depicted) configured to move the water through channel of fluid communication 536 to water source 562. In the depicted embodiment, an electrolytic element 534 in water reservoir 531 electrolyzes water to produce hypochlorous acid. Alternatively or additionally, a UV lamp 532 in water reservoir 531 provides UV radiation. In some embodiments hypochlorous acid and/or UV irradiation contribute to a reduction in biologically active contaminants and/or VOCs in water in reservoir 531. In other exemplary embodiments of the invention hypochlorous acid is added to water in reservoir 531 from an external source.

In some embodiments cooling unit 565 includes a heat pump which can remove moisture from the air. Optionally, water source 562 returns some or all of this moisture.

Other features of system 501 are as described for system 500 (FIG. 2A).

Figure 2C:
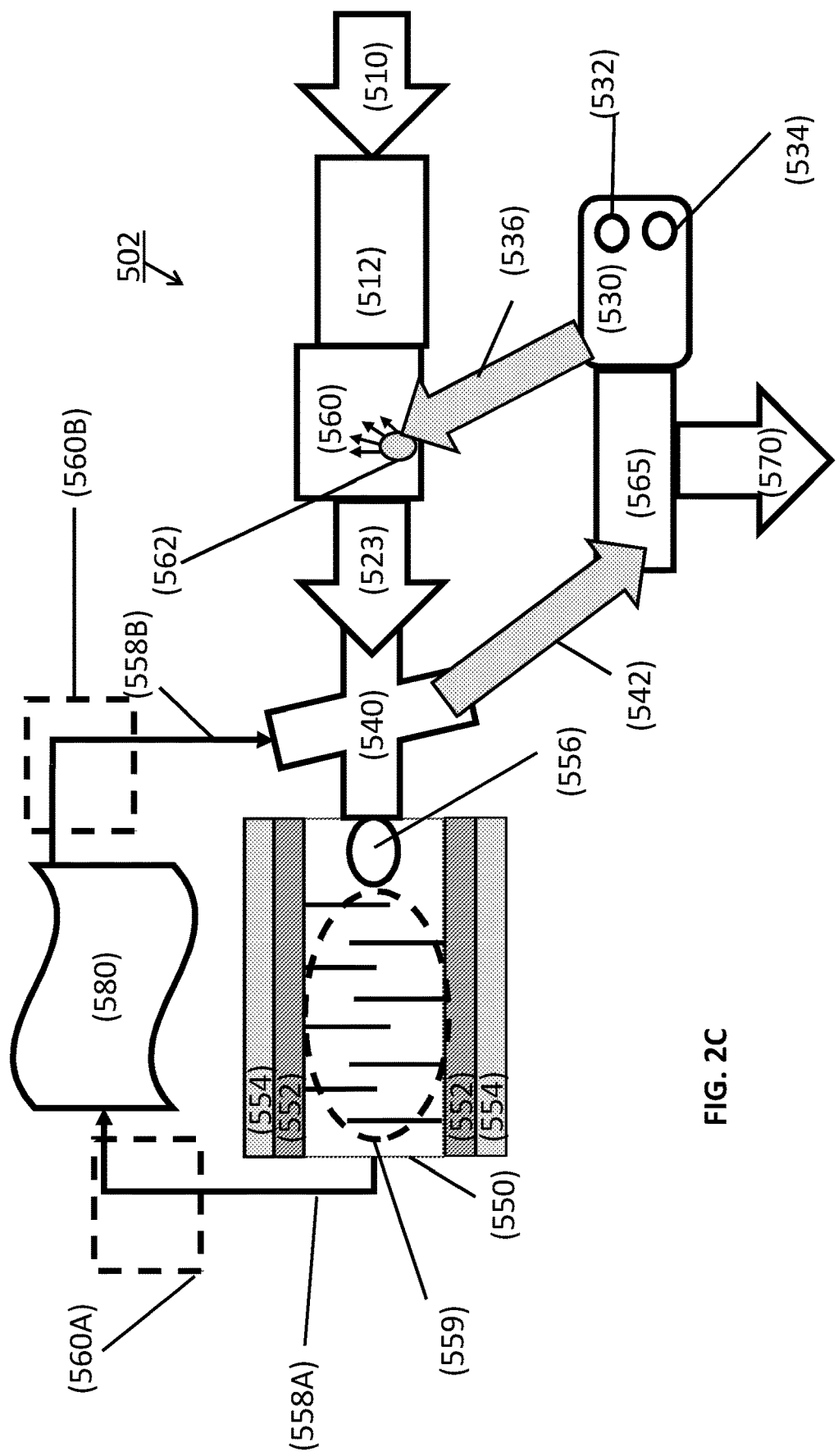
FIG. 2C is a simplified schematic representation of an air purification system according to some further additional exemplary embodiments of the invention.

FIG. 2C is a simplified schematic representation of an air purification system, indicated generally as 502, according to some further additional exemplary embodiments of the invention. Depicted exemplary system 502 is identical to system 501 of FIG. 2B except that:

Evaporative cooler 560 is positioned to receive said initial air stream as it exits fan 512. In the depicted embodiment, condensate collector pan 530 replaces the water reservoir 531 of FIG. 2B. Condensate collector pan 530 collects condensed water produced by cooling unit 565. As in FIG. 2B, a pump, not depicted, moves the water through channel of fluid communication 536 to water source 562. As in FIG. 2A, purification of water in pan 530 is by UV light source 532 and/or by electrolytic element 534 which produces hypochlorous acid from salt in the water.

Alternatively or additionally, in some embodiments a fan is positioned at 542. According to these embodiments, the fan "pulls" air from heat exchanger 540 and this negative pressure is transmitted all the way back to 523.

Systems 501 and/or 502 (FIG. 2B and FIG. 2C respectively) are characterized by lower energy consumption than system 500 (FIG. 2A). Much of the energy savings results from elimination of the dehumidifier 520 (FIG. 2A). Cooling unit 565 (e.g. a heat pump) (FIG. 2B) consumes less energy than a dehumidifier. Alternatively or additionally, fan 512 (FIG. 2B) is smaller than dehumidifier 520 (FIG. 2A) contributing to reduction in overall system size. Alternatively or additionally, system 501 can be implemented without water treatment.

On the other hand, implementation of system 501 without option water source 562 precludes use of hypochlorous acid and/or contributes to an increase in difficulty of achieving RH in 570 comparable to 510. Alternatively or additionally, implementation of cooling unit 565 contributes to an increase in overall system size as the evaporative cooler 560 of system 500 (FIG. 2A) is smaller than a heat pump.

Referring again to FIG. 2B and FIG. 2C concurrently, in some embodiments air to air heat exchanger 540 preheats the initial airstream 523 from room temperature to at least 150° C. within 1 second. Alternatively or additionally, in some embodiments heater 550 (denaturation chamber) heats the initial airstream to at least 200° C. within 0.5 seconds to 1 second. Alternatively or additionally, in some embodiments heater 550 heats the initial airstream 523 (after it passes through heat exchanger 540) to at least 350° C. within 1 second. Alternatively or additionally, in some embodiments heated air stream 558B passing through heat exchanger 540 is cooled within 1 second as it heats initial airstream 523. Alternatively or additionally, in some embodiments heater 550 has a retention time of at least 5 seconds. Since retention time equals compartment size divided by flow rate, a retention time of at least 5 seconds indicates that the denaturation chamber has a size of at least 1388 $cm^3$ per cubic meter/hour of air in the initial air stream.

In some embodiments baffles 559 contribute to an increase in retention time. Alternatively or additionally, in some embodiments heated air stream 558A output by heater 550 arrives at heat exchanger 540 at least 2 seconds after exiting the heater (see 558B).

First Exemplary Method

Figure 3:
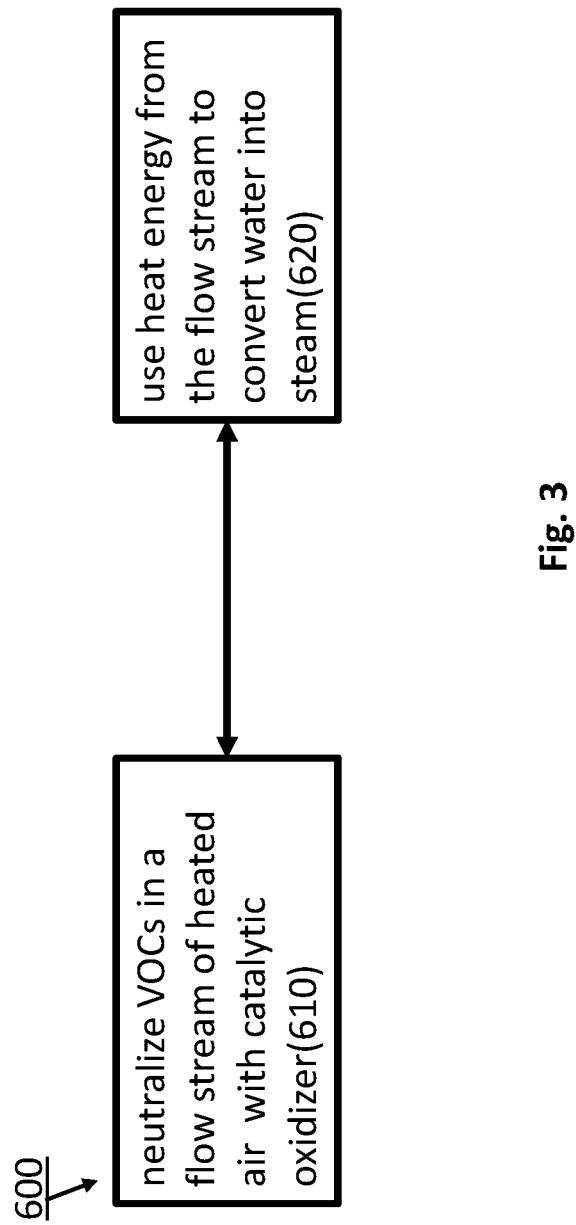
FIG. 3 is a simplified flow diagram of a method according to some embodiments of the invention.

FIG. 3 is a simplified flow diagram of a method, indicated generally as 600, according to some embodiments of the invention.

In the depicted embodiment, method 600 includes neutralizing 610 volatile organic compounds in a flow stream of heated air with a catalytic oxidizer and using 620 heat energy from the flow stream to convert water into steam. In some embodiments the heated air stream is pressurized. In some embodiments the stream of heated air is pressurized to at least 1.9 atmospheres. Stream 184 in FIG. 1A and FIG. 1B as well as streams 558A/558B and 542 in FIG. 2A are examples of stream treated using method 600.

According to various exemplary embodiments of the invention 610 comes before 620 or 620 comes before 610. In some embodiments, hypochlorous acid in the water further contributes to a reduction in VOCs in the flow stream.

Second Exemplary Method

Figure 4A:
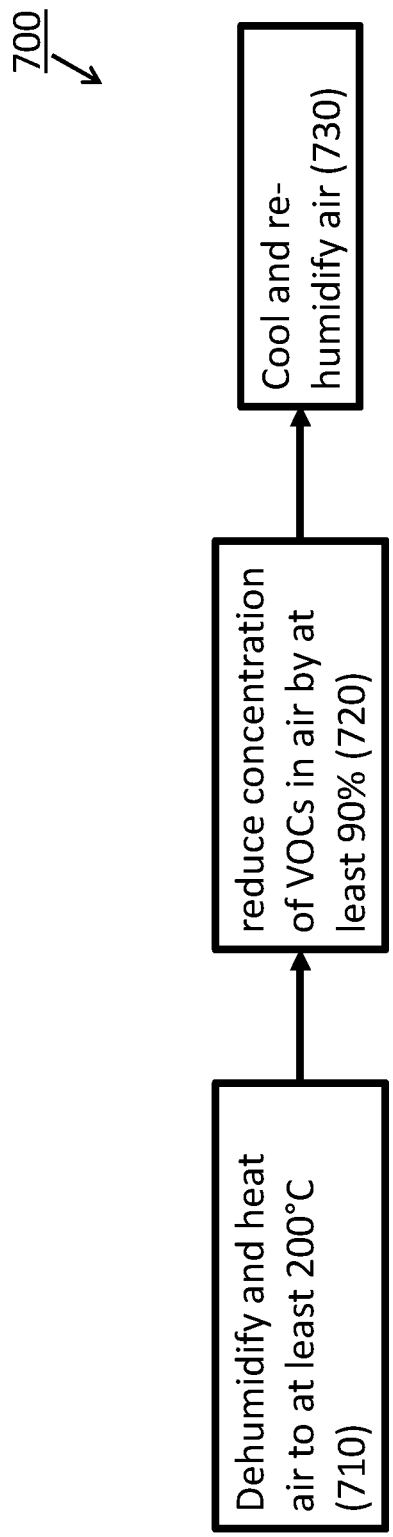
FIG. 4A is a simplified flow diagram of an additional method according to some embodiments of the invention.

FIG. 4A is a simplified flow diagram of an additional method, indicated generally as 700, according to some embodiments of the invention.

In the depicted embodiment, method 700 includes dehumidifying 710 and heating air to a temperature of at least 200° C., reducing 720 a concentration of VOCs in the air by at least 90% and cooling 730 and re-humidifying the air.

As described above in the context of FIGS. 1A, 1B and 2, reducing 720 a concentration of VOCs in the air can be accomplished using a catalytic oxidizer (e.g. 480; 580) and/or an aqueous solution of hypochlorous acid.

Alternatively or additionally, as described above in the context of FIGS. 1A, 1B and 2, once air is heated to a temperature of at least 200° C., it may be retained at that temperature for 5 seconds or more (e.g. in pressure tank 180 of FIGS. 1A and 1B or denaturation chamber 550 of FIG. 2)

Method 700 typically employs ambient air at a temperature of 20° C. to 25° C. with 40% RH to 60% RH as an input at 710. In some embodiments RH is lowered to 5% to 30% at 710.

At 730 air is typically cooled to 15° C. to 25° C. and/or returned to RH of 40% to 60%.

Third Exemplary Method

Figure 4B:
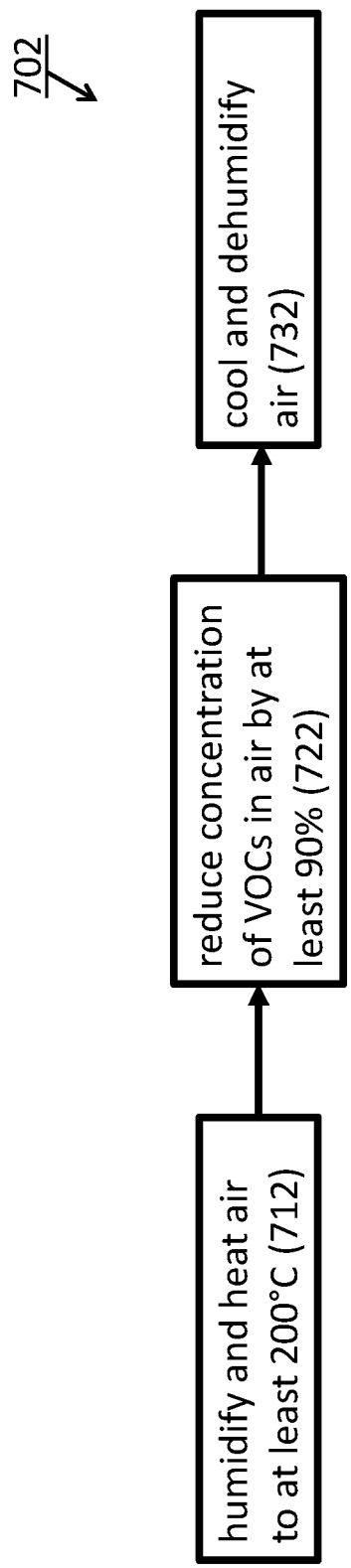
FIG. 4B is a simplified flow diagram of an additional method according to some embodiments of the invention.

FIG. 4B is a simplified flow diagram of an additional method, indicated generally as 702, according to some embodiments of the invention.

In the depicted embodiment, method 702 includes humidifying 712 and heating air to a temperature of at least 200° C., reducing 722 a concentration of VOCs in the air by at least 90% and cooling 732 and dehumidifying the air.

As described above in the context of FIGS. 1A, 1B and 2A, 2B and 2C, reducing 720 a concentration of VOCs in the air can be accomplished using a catalytic oxidizer (e.g. 480 or 580) and/or an aqueous solution of hypochlorous acid.

Alternatively or additionally, as described above in the context of FIGS. 1A, 1B and 2, once air is heated to a temperature of at least 200° C., it may be retained at that temperature for 5 seconds or more (e.g. in pressure tank 180 of FIGS. 1A and 1B or denaturation chamber 550 of FIG. 2)

Method 702 typically employs ambient air at a temperature of 20° C. to 25° C. with 40% RH to 60% RH as an input at 712. In some embodiments RH is increased to 70% to 75% at 712. At 732 air is typically cooled to 15° C. to 25° C. and/or returned to RH of 40% to 60%.

Fourth Exemplary Method

Figure 5:
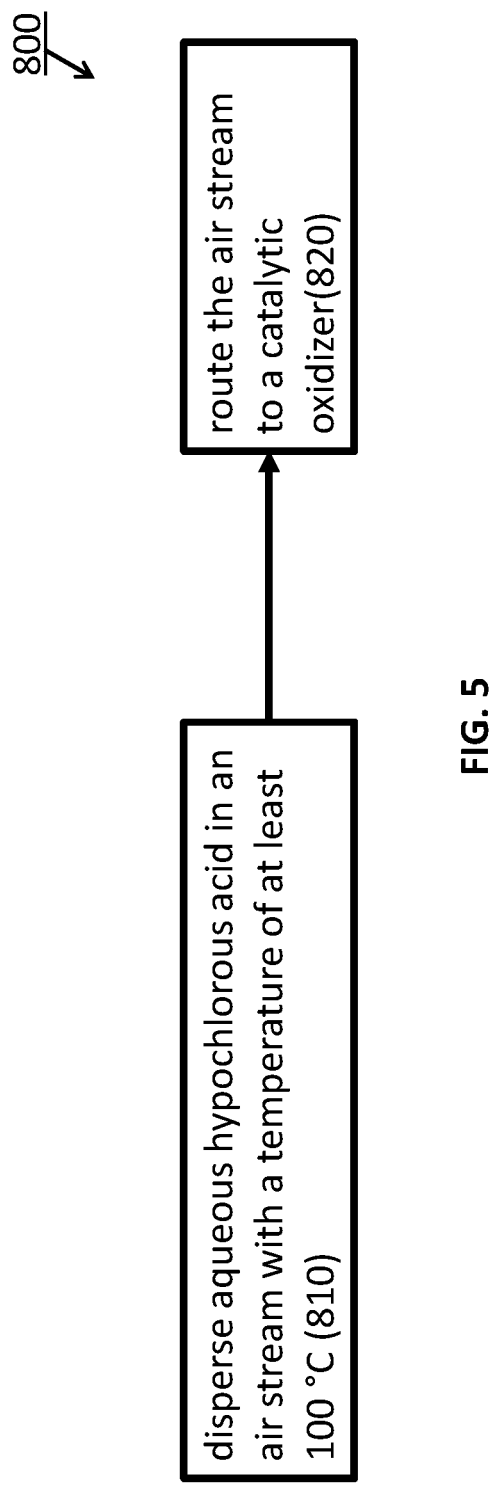
FIG. 5 is a simplified flow diagram of an additional method according to some embodiments of the invention.

FIG. 5 is a simplified flow diagram of an additional method, indicated generally as 800, according to some embodiments of the invention. Depicted exemplary method 800 includes dispersing 810 aqueous hypochlorous acid in an air stream with a temperature of at least 100° C. and routing 820 said air stream to a catalytic oxidizer.

Additional Exemplary Method

Figure 6:
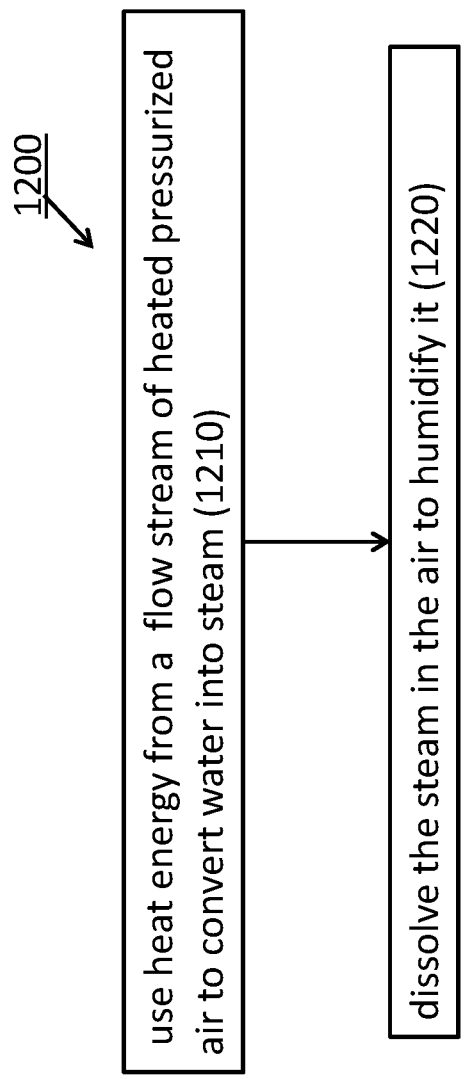
FIG. 6 is a simplified flow diagram of a method according to some embodiments of the invention.

FIG. 6 is a simplified flow diagram of a method for air treatment, indicated generally as 1200, according to some embodiments of the invention. Depicted exemplary method 1200 includes using 1210 heat energy from a flow stream of heated pressurized air to convert water into steam and dissolving 1220 the steam in the air to humidify it. In some embodiments the pressurized air is cooled by evaporation of water sprayed into it.

Additional Exemplary System

Figure 7:
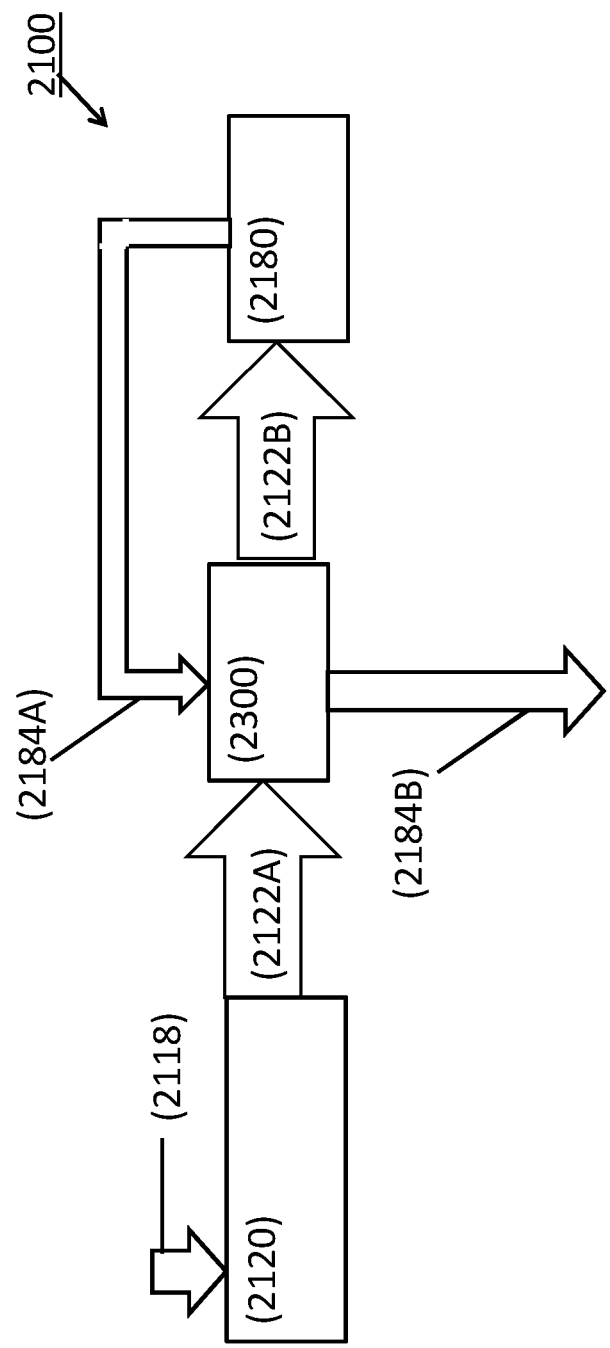
FIG. 7 is simplified schematic representation of an air purification system according to some exemplary embodiments of the invention.

FIG. 7 is an exemplary air purification system indicated generally as 2100.

In the depicted embodiment, system 2100 includes a compressor 2120 providing a first output flow 2122A of pressurized air at a first temperature and a pressure tank 2180 providing a second output flow 2184A of pressurized air at a second higher temperature. Compressor 2120 pressurizes ambient air 2118.

Depicted exemplary system 2100 also includes an air to air heat exchanger 2300 designed and configured to heat first output flow 2122A using heat from said second output flow 2184A. As a result flow 2184B is at a lower temperature than flow 2184A and flow 2122B is at a higher temperature than flow 122A.

In some exemplary embodiments of the invention, the temperature of 2122B is 40° C. to 100° C. greater than 2122A. Alternatively or additionally, in some embodiments the temperature of 2184B is 50° C. to 100° C. less than the temperature of 2184A.

In some embodiments the first temperature of flow 2122A is ambient temperature plus 30° C. to 50° C. In some of these embodiments dehumidification contributes to a decrease in the temperature of flow 2122A.

In other exemplary embodiments of the invention, the first temperature of flow 2122A is 120° C. to 180° C. at the exit of compressor 2120. Alternatively or additionally, in some embodiments the second temperature of flow 2184A is 170° C.; 180° C.; 190° C.; 200° C.; 210° C.; 220° C.; 230° C.; 240° C.; 250° C. or intermediate or higher temperatures.

According to various exemplary embodiments of the invention flow 2122A has a pressure of 1.9 atmospheres; 3 atmospheres; 4 atmospheres; 5 atmospheres; 6 atmospheres; 7 atmospheres; 8 atmospheres; 9 atmospheres; 10 atmospheres or intermediate pressures. In some embodiments flow 2122 has a pressure of 8 to 10 atmospheres. Although flow 2122 is depicted as an arrow, it is typically directed by a pipe or other conduit to pressure tank 2180. In the depicted embodiment, compressor 2120 draws in ambient air 2118, which carries one or more types of impurities (For example virus particles and/or bacteria).

In the depicted embodiment, system 2100 includes a pressure tank 2180 which receives output flow 2122 of pressurized air and heats the air while maintaining pressure. In some exemplary embodiments of the invention, pressure tank 2180 heats the air to a temperature of 170° C.; 180° C.; 190° C.; 200° C.; 210° C.; 220° C.; 230° C.; 240° C.; 250° C. or intermediate or higher temperature. Alternatively or additionally, in some embodiments pressure tank 2180 heats the air to a target temperature for 1 seconds, 2 seconds, 3 seconds, 4 seconds, 5 seconds, 6 seconds, 7 seconds, 8 seconds, 9 seconds, 10 seconds, 11 seconds, 12 seconds, 20 seconds, 30 seconds, 40 seconds, 50 seconds, or 60 seconds or intermediate or longer amounts of time.

In some exemplary embodiments of the invention, the air to air heat exchanger 2300 preheats pressurized air 2122A from room temperature to at least 150° C.; 160° C.; 170° C.; 180° C. or intermediate or higher temperatures within 1 second. Alternatively or additionally, in some embodiments the pressure tank 2180 heats pressurized airstream 2122B to at least 200° C. within 0.5 seconds to 1 second. Alternatively or additionally, in some embodiments pressure tank 2180 heats pressurized airstream 2122B to at least 350° C. within 1 second. Alternatively or additionally, in some embodiments heated air stream 2184A passing through heat exchanger 2300 is cooled within 1 second as it heats pressurized airstream 2122A. Alternatively or additionally, in some embodiments pressure tank 2180 has a retention time of at least 5 seconds. In some embodiments baffles in pressure tank 2180 contribute to an increase in retention time. Alternatively or additionally, in some embodiments heated air stream 2184A output by pressure tank 2180 arrives at heat exchanger 2300 at least 2 seconds after it exits tank 2180.

Further Additional Exemplary Method

In some exemplary embodiments of the invention there is provided a method including pressurizing airstreams directed to an air to air heat exchanger in an air treatment system. According to various exemplary embodiments of the invention the air is pressurized to a pressure of at least 1.9 atmospheres, at least 4 atmospheres, at least 6 atmospheres, at least 8 atmospheres, at least 10 atmospheres, at least 12 atmospheres, or intermediate or higher pressures.

Further Additional Exemplary System

Figure 8:
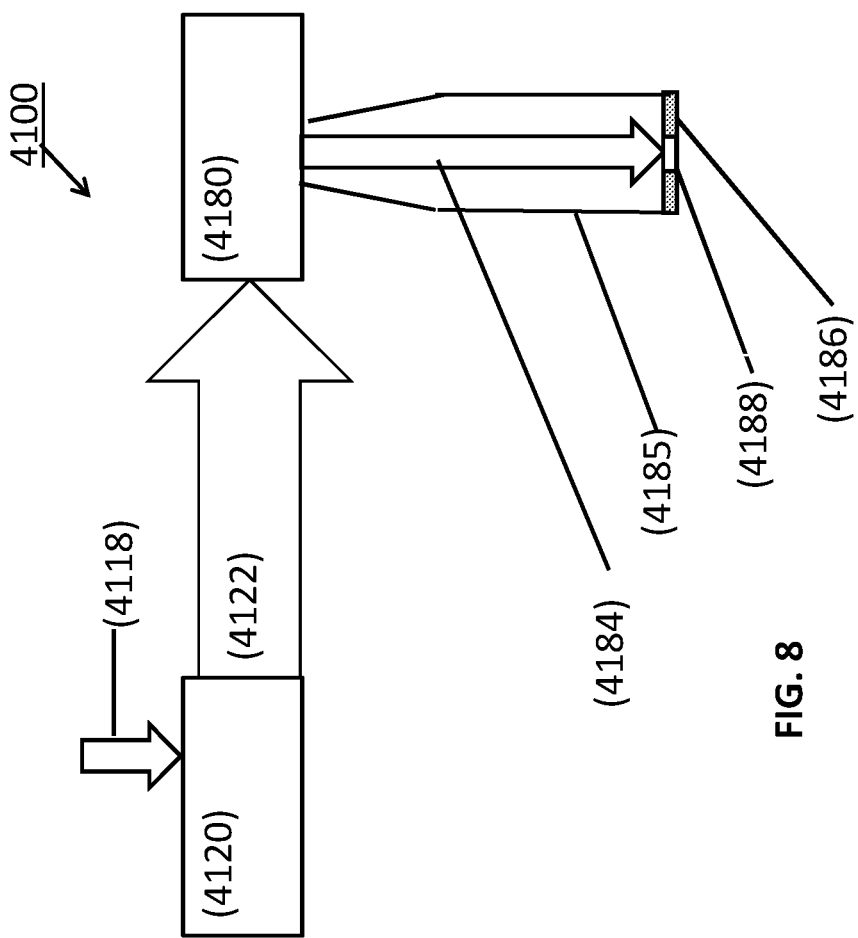
FIG. 8 is simplified schematic representation of an air purification system according to some exemplary embodiments of the invention.

FIG. 8 is simplified schematic representation of an air purification system, indicated generally as 4100, according to some exemplary embodiments of the invention.

Depicted exemplary system 100 includes An air purification system comprising a compressor 4120 providing an output flow 4122 of pressurized air to a pressure tank 4180. Tank 4180 receives the air and heats it while maintaining pressure. In the depicted embodiment, compressor 4120 compresses ambient air 4118.

According to various exemplary embodiments of the invention flow 4122 has a pressure of 1.9 atmospheres; 3 atmospheres; 4 atmospheres; 5 atmospheres; 6 atmospheres; 7 atmospheres; 8 atmospheres; 9 atmospheres; 10 atmospheres or intermediate pressures. In some embodiments flow 4122 has a pressure of 8 to 10 atmospheres. Although flow 4122 is depicted as an arrow, it is typically directed by a pipe or other conduit to pressure tank 4180. In the depicted embodiment, compressor 4120 draws in ambient air 4118, which carries one or more types of impurities (For example virus particles and/or bacteria).

In the depicted embodiment, system 4100 includes a pressure tank 4180 which receives output flow 122 of pressurized air and heats the air while maintaining pressure. In some exemplary embodiments of the invention, pressure tank 4180 heats the air to a temperature of 170° C.; 180° C.; 190° C.; 200° C.; 210° C.; 220° C.; 230° C.; 240° C.; 250° C. or intermediate or higher temperature. Alternatively or additionally, in some embodiments pressure tank 4180 heats the air to a target temperature for 1 seconds, 2 seconds, 3 seconds, 4 seconds, 5 seconds, 6 seconds, 7 seconds, 8 seconds, 9 seconds, 10 seconds, 11 seconds, 12 seconds, 20 seconds, 30 seconds, 40 seconds, 50 seconds, or 60 seconds or intermediate or longer amounts of time.

In the depicted embodiment, the system includes a release manifold 4185 having a partially closed end 4186 including an orifice 4188. In the depicted embodiment, manifold 4185 is in fluid communication with pressure tank 4180.

In some exemplary embodiments of the invention, orifice 4188 obviates a need for an expansion valve on tank 4180. In some embodiments orifice 4188 contributes to reliability of the system because it has no moving parts. Optionally, orifice 4188 contributes to a reduction in cost of producing and/or maintaining the system. Alternatively or additionally, in some embodiments a diameter of orifice 4188 governs flow rate of exit stream 4184 out of the system.

Alternatively or additionally, in some embodiments exit of air stream 4184 via orifice 4188 causes a reduction in pressure and reduction in temperature. According to these embodiments, heat energy is transformed to kinetic energy as volume increases. According to various exemplary embodiments of the invention exit of stream 4184 through orifice 4188 is to ambient conditions or to a climate control.

In some embodiments a temperature of output flow stream 4184 as it exits tank 4180 is at least 100° C.; at least 110° C., least 120° C.; at least 130° C. least 140° C.; at least 150° C. least 160° C.; at least 170° C. least 180° C.; at least 190° C. least 200° C.; at least 210° C. least 220° C.; at least 230° C. least 240° C.; at least 250° C. least 260° C.; at least 270° C. least 100° C.; at least 280° C. least 290° C.; at least 300° C. or intermediate or greater temperatures. Alternatively or additionally, in some embodiments a pressure of output flow stream 4184 as it exits tank 4180 is at least 1.9 atmospheres; at least 3 atmospheres; at least 4 atmospheres, at least 5 atmospheres, at least 6 atmospheres, at least 7 atmospheres, at least 8 atmospheres, at least 9 atmospheres, at least 10 atmospheres or intermediate or greater pressures.

In some embodiments manifold 4185 cools the stream to 35° C., 40° C., 45°, 50° C., 60° C., 70° C., 80° C., or intermediate or lower temperatures. In some embodiments cooling includes injection of water into the stream.

In some embodiments after stream 4184 exits orifice 188 its temperature drops to 34° C., 32° C., 30° C., 29° C., 27° C., 25° C., 20° C., 18° C. or intermediate or lower temperatures. Alternatively or additionally, in some embodiments the pressure of stream 4184 after it exits orifice 188 is reduced to ambient pressure.

In some embodiments stream 4184 expands as it passes through orifice 188. Optionally, expansion causes water dissolved in stream 4184 to evaporate contributing to an increase in relative humidity level in the air. In some embodiments this increase in relative humidity contributes to cooling of the air. According to various exemplary embodiments of the invention the relative humidity in stream 4184 just after it leaves orifice 4188 is 40% to 60%.

According to various exemplary embodiments of the invention a diameter of manifold 4185 is smaller or larger than tank 4180. Alternatively or additionally, in some embodiments there is an additional orifice (not depicted) between tank 4180 and manifold 4185 to create two expansion stages. Alternatively or additionally, in some embodiments manifold 4185 maintains the same pressure tank 4180 and expansion of stream 4184 occurs only after exit from orifice 4188 at the manifold end. In some embodiments manifold size is zero and orifice 4188 is provided in a wall of tank 1480.

Further Additional Exemplary Method

In some exemplary embodiments of the invention, there is provided a method including routing a pressurized air stream at a temperature of at least 30° C. through a fixed diameter orifice. Optionally, passage through the orifice cools the stream. According to various exemplary embodiments of the invention the temperature of the stream prior to passage through the orifice is 35° C., 40° C., 45°, 50° C., 60° C., 70° C., 80° C., or intermediate or lower temperatures. In some embodiments water injected into the air in the manifold contributes to a temperature reduction. Alternatively or additionally, according to various exemplary embodiments of the invention passage through the orifice cools the stream to 34° C., 32° C., 30° C., 29° C., 27° C., 25° C., 20° C., 18° C. or lesser or intermediate temperatures.

Alternatively or additionally, in some embodiments water in the air stream vaporizes as during expansion. In some embodiments vaporization helps control humidity level and/or lower temperature.

Exemplary Flow Considerations

Systems 400, 401 and 500 and/or methods 600 and 700 are scalable to different use scenarios. For example, purification of air in a small space, such as the interior of a car, might employ a flow rate of 12 m3/h (200 L/M). For a large space, such as a lobby area of a building, a dining hall, a factory or a transportation terminal (e.g. airport or train station), purification of air might employ a flow rate of 10000 m3/h of air.

In addition, to the total volume being treated, other factors contribute to selection of flow rate. For example, a municipal bus during rush hour might require a higher flow rate than the same bus at off peak hours when it is only 20% occupied.

Exemplary Insulation Considerations

According to various exemplary embodiments of the invention insulation covers various pipes and/or conduits and/or pressure tank 180 and/or oxidizer 480 or 580 in the relevant system. In some embodiments insulation contributes to an increase in heat retention.

Exemplary Theoretical Considerations

According to some exemplary embodiments of the invention described hereinabove, denaturation of proteins in biological contaminants inactivates them.

Alternatively or additionally, in some embodiments heat and/or pressure changes the morphology of allergens so the immune system doesn't recognize them.

Three factors contribute to denaturation effectiveness: temperature, time, and pressure. There are synergies between these three factors so that one can be reduced while increasing another to maintain denaturation effectiveness.

For example, when air reaches "working parameters" (typically defined in terms of pressure and temperature) a certain amount of time is needed to achieve a desired degree of denaturation. In some embodiments valves are used to maintain a desired pressure.

Residence time is determined by the size of a compartment within the system.

Pressurized systems (as depicted in FIG. 1A and FIG. 1B) shorten the time needed to achieve a desired degree of denaturation at a given temperature. Because the air is pressurized, the size of the chamber needed for treatment is reduced. For example, treating 10 cubic meters of ambient air at 2.5 atmospheres requires a pressurized chamber of only 4 cubic meters. In addition, the increase in pressure contributes to a reduction in required residence time in the chamber. The reduction in required residence time contributes to a further reduction in the required chamber size.

However, air compression is characterized by a high energy cost. As a result pressurized systems (as depicted in FIG. 1A and FIG. 1B) can cost more in terms of capital expenditure and/or operating costs than non-pressurized systems (as depicted in FIG. 2A and/or FIG. 2B) with similar capacity.

A non-pressurized system (as depicted in FIG. 2A and/or FIG. 2B) working at the same temperature as a pressurized system (as depicted in FIG. 1A and FIG. 1B) compensates the absence of high pressure with a longer treatment time.

If the longer treatment time is achieved with increased residence time in a treatment compartment, compartment size will need to increase to accommodate the required air volume at the operational flow rate.

However, non-pressurized systems (of the type depicted in FIGS. 2A and/or 2B) are less expensive in terms of operational energy so a non-pressurized system will cost less in terms of capital expenditure and/or operational cost.

Weighing these considerations against one another, small pressurized systems with low air throughput, such as home systems, are feasible. The difference in total cost is negligible (though high in percentage) and is balanced by the savings in space for installation.

Large systems with high air throughput, such as commercial systems (e.g. factories, schools, office buildings, hospitals), are more amenable to implementation of non-pressurized systems (as depicted in FIG. 2A and/or FIG. 2B). For these large scale systems, the cost savings is high in both absolute terms and as a percentage, and space for installation is less problematic.

Exemplary Use Scenario: Commercial Airliner

Commercial airliners hold hundreds of people in close proximity to one another for hours. During this time, air in the passenger cabin is recycled many times and spread across the cabin so one sick person coughing or sneezing can spread airborne pathogens, such as viruses throughout the passenger cabin. Because commercial airliners fly at high altitudes, ambient pressure outside the aircraft is below 1 atmosphere and ambient temperature outside the aircraft is typically below freezing. The passenger cabin is typically pressurized to one atmosphere and heated to 15° C. to 20° C. for passenger comfort and safety.

Unpressurized compartments (e.g. cargo hold) in an airliner are un-heated. According to various exemplary embodiments of the invention hot air streams are discharged into unpressurized compartments and/or outside the aircraft.

Alternatively or additionally, in some embodiments a small amount of cold air from unpressurized compartments and/or outside the aircraft is mixed with heated sterilized air produced by the system to cool it prior to return to the passenger cabin. In light of these considerations, implementation of an unpressurized system (as depicted in FIG. 2A and/or FIG. 2B) in the context of a commercial airliner is believed feasible. As discussed above systems of this type are amenable to high throughput implementations.

Currently, air the climate control system is drawn from one place and returned at many places (typically in small ceiling mounted vents over each individual passenger seat). In some exemplary embodiments of the invention, the direction of airflow in the system is reversed. According to these embodiments of the invention, contaminated air is drawn out of the passenger compartment through the small ceiling mounted vents over each individual passenger seat and treated air is delivered from one, or a few, large vents.

In some exemplary embodiments of the invention, a version of low pressure system 500 (FIG. 2A) or 501 (FIG. 2B) is employed in an airliner. For example, in some embodiments only enough heat to activate catalytic oxidizer 580 is applied by heating elements 552 and/or 556. A water delivery mechanism 562 positioned at 560A delivers water containing hypochlorous acid. The hypochlorous acid neutralizes airborne pathogens (e.g. COVID 19 virions). The hypochlorous acid is deactivated by catalytic oxidizer 580 so that airstream 5586 is substantially pathogen free. In some embodiments this system employs the reversed airflow strategy described above.

Exemplary Use Scenario: Office Building

Many modern buildings are closed environments, with windows that do not open and few openings to the outside environment.

During office hours, commercial buildings are filled with many people.

Due to low replacement of air, contaminants, both biological and gases released by VOCs linger and accumulate within the building.

In light of these considerations, implementation of an unpressurized system (as depicted in FIG. 2A) in the context of a commercial office building is believed feasible. As discussed above systems of this type are amenable to high throughput implementations.

It is expected that during the life of this patent many compressor types and pump types and water delivery mechanism types will be developed and the scope of the invention is includes all such new technologies a priori.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specifically, a variety of numerical indicators have been utilized. It should be understood that these numerical indicators could vary even further based upon a variety of engineering principles, materials, intended use and designs incorporated into the various embodiments of the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce additional embodiments of the invention. The examples given above are exemplary in nature and are not intended to limit the scope of the invention which is defined solely by the following claims. Each recitation of an embodiment of the invention that includes a specific feature, part, component, module or process is an explicit statement that additional embodiments of the invention not including the recited feature, part, component, module or process exist.

Alternatively or additionally, various exemplary embodiments of the invention exclude any specific feature, part, component, module, process or element which is not specifically disclosed herein.

Specifically, the invention has been described in the context of air purification systems but might also be used in the context of humidity control systems.

All publications, references, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

The invention claimed is:

1. A system comprising:

(a) a fan directing an initial air stream to a denaturation chamber which heats said initial airstream to a temperature of 200° C. and not more than 225° C. at ambient pressure and outputs a heated air stream at ambient pressure; and (b) an air to air heat exchanger positioned and configured to use said heated air stream to preheat said initial airstream prior to its arrival at said denaturation chamber;

wherein said denaturation chamber has a retention time of at least 5 seconds;

wherein said denaturation chamber does not contain a catalyst; and wherein the system does not include a filter.

2. The system according to claim 1, wherein said initial air stream and said heated air stream output by said heater of said denaturation chamber are each continuous air streams.

3. The system according to claim 1, comprising a cooling unit positioned to further cool said heated air stream after it passes through said air to air heat exchanger.

4. The system according to claim 3, wherein said cooling unit includes one or more functional elements selected from the group consisting of: a heat pump, an active heat exchanger, and a passive heat exchanger.

5. The system according to claim 3, comprising:

an evaporative cooler comprising a water source, wherein said evaporative cooler is positioned to receive said heated air stream.

6. The system according to claim 5, wherein said evaporative cooler is positioned to receive said heated air stream after said heated air stream has passed through said air to air heat exchanger.

7. The system according to claim 5, wherein said evaporative cooler is positioned to receive said initial air stream as it exits said fan.

8. The system according to claim 1, comprising:
a catalytic oxidizer positioned between an exit of said denaturation chamber and said air to air heat exchanger so that said heated air stream flows through said catalytic oxidizer producing a VOC reduced hot air stream.

9. The system according to claim 5, comprising:
a channel of fluid communication routing water from a water reservoir to said water source; and
a pump configured to move said water through said channel of fluid communication to said water source.

10. The system according to claim 9, comprising an electrolytic element in said water reservoir.

11. The system according to claim 5, comprising:
a source of hypochlorous acid connected to said water source.

12. The system according to claim 1, wherein said air to air heat exchanger preheats said initial airstream from room temperature to at least 150° C. within 1 second.

13. The system according to claim 12, wherein said denaturation chamber heats said initial airstream to at least 200° C. within 0.5 seconds to 1 second.

14. The system according to claim 1, wherein said heat exchanger is sized so that said heated air stream passes through said heat exchanger within 1 second.

15. The system according to claim 1, wherein said denaturation chamber comprises baffles.

16. The system according to claim 1, wherein a flow path of said heated air stream output by said denaturation chamber is sufficiently long such that said heated air stream output by said denaturation chamber arrives at said heat exchanger after at least 2 seconds.

17. A system consisting essentially of:
(a) a fan directing an initial air stream to a denaturation chamber which heats said initial airstream to a temperature of at least 200° C. at ambient pressure and not more than 225° C. at ambient pressure and outputs a heated air stream; and
(b) an air to air heat exchanger positioned and configured to use said heated air stream to preheat said initial airstream prior to its arrival at said denaturation chamber;
wherein said denaturation chamber has a retention time of at least 5 seconds; and
wherein said denaturation chamber does not contain a catalyst.

18. A system comprising:
(a) a fan directing an initial air stream to a denaturation chamber which heats said initial airstream to a temperature of 200° C. and not more than 225° C. at ambient pressure and outputs a heated air stream at ambient pressure; and
(b) an air to air heat exchanger positioned and configured to use said heated air stream to preheat said initial airstream prior to its arrival at said denaturation chamber;
wherein said denaturation chamber has a retention time of at least 5 seconds; and
wherein said denaturation chamber does not contain a catalyst.

* * * * *